US010881475B2

(12) United States Patent
Kan

(10) Patent No.: US 10,881,475 B2
(45) Date of Patent: Jan. 5, 2021

(54) SURGICAL ROBOT

(71) Applicant: KAWASAKI JUKOGYO KABUSHIKI KAISHA, Kobe (JP)

(72) Inventor: Kazutoshi Kan, Kobe (JP)

(73) Assignees: KAWASAKI JUKOGYO KABUSHIKI KAISHA, Kobe (JP); MEDICAROID CORPORATION, Kobe (JP)

(*) Notice: Subject to any disclaimer, the term of this patent is extended or adjusted under 35 U.S.C. 154(b) by 319 days.

(21) Appl. No.: 15/742,905

(22) PCT Filed: Jul. 9, 2015

(86) PCT No.: PCT/JP2015/003487
§ 371 (c)(1),
(2) Date: Jan. 9, 2018

(87) PCT Pub. No.: WO2017/006376
PCT Pub. Date: Jan. 12, 2017

(65) Prior Publication Data
US 2018/0214226 A1 Aug. 2, 2018

(51) Int. Cl.
A61B 34/00 (2016.01)
B25J 17/02 (2006.01)
(Continued)

(52) U.S. Cl.
CPC ............ A61B 34/71 (2016.02); A61B 17/29 (2013.01); A61B 34/35 (2016.02); A61B 34/37 (2016.02);
(Continued)

(58) Field of Classification Search
CPC ........... B25J 17/02; B25J 18/06; A61B 34/71; A61B 17/29; A61B 34/37; A61B 34/35;
(Continued)

(56) References Cited

U.S. PATENT DOCUMENTS 6,246,200 B1* 6/2001 Blumenkranz ........ B25J 9/1689
128/DIG. 7
6,676,684 B1 1/2004 Morley et al.
(Continued)

FOREIGN PATENT DOCUMENTS

CN 103358304 A 10/2013
EP 1 915 966 A1 4/2008
(Continued)

OTHER PUBLICATIONS

Oct. 6, 2015 International Search Report issued in International Patent Application No. PCT/JP2015/003487.

Primary Examiner — Phong Son H Dang
(74) Attorney, Agent, or Firm — Oliff PLC

(57) ABSTRACT

A robot main body driving mechanism including wrist joint driving portion; and robot main body including base detachably fixed to robot main body driving mechanism, arm including hollow shaft and wrist joint, shaft including proximal end continuous with base, wrist joint being continuous with distal end of shaft, wrist joint rotating around axis of distal end of arm, end effector attached to wrist joint, and wrist joint driving force transmission portion including hollow torque transmission tube, torque transmission tube being inserted through shaft and including distal end attached to wrist joint, wherein: by attaching base to robot main body driving mechanism, wrist joint driving portion is connected to proximal end of torque transmission tube to rotate torque transmission tube around axis of torque transmission tube; and by detaching base from robot main body driving mechanism, wrist joint driving portion is separated from torque transmission tube.

12 Claims, 12 Drawing Sheets

(51) Int. Cl.
*B25J 18/06* (2006.01)
*A61B 34/37* (2016.01)
*A61B 17/29* (2006.01)
*A61B 34/35* (2016.01)
*A61B 90/57* (2016.01)
*A61B 34/30* (2016.01)
*A61B 17/00* (2006.01)

(52) U.S. Cl.
CPC ............... *B25J 17/02* (2013.01); *B25J 18/06* (2013.01); *A61B 2017/00039* (2013.01); *A61B 2017/00199* (2013.01); *A61B 2017/00212* (2013.01); *A61B 2017/00398* (2013.01); *A61B 2017/00477* (2013.01); *A61B 2017/2929* (2013.01); *A61B 2017/2932* (2013.01); *A61B 2034/301* (2016.02); *A61B 2034/305* (2016.02); *A61B 2090/571* (2016.02)

(58) Field of Classification Search
CPC .... A61B 2034/301; A61B 2017/00212; A61B 2017/00477; A61B 2017/00039; A61B 2017/2932; A61B 2017/00398; A61B 2017/00199; A61B 2034/305; A61B 2017/2929; A61B 2090/571
See application file for complete search history.

(56) References Cited

U.S. PATENT DOCUMENTS

| | | |
|---|---|---|
| 2002/0128552 A1 | 9/2002 | Nowlin et al. |
| 2003/0135204 A1* | 7/2003 | Lee .................... A61B 17/0469 606/1 |
| 2004/0092912 A1 | 5/2004 | Jinno et al. |
| 2004/0199147 A1* | 10/2004 | Nishizawa ........... A61B 17/062 606/1 |
| 2007/0119274 A1* | 5/2007 | Devengenzo ......... A61B 34/71 74/490.01 |
| 2007/0197896 A1 | 8/2007 | Moll et al. |
| 2007/0260114 A1 | 11/2007 | Miyamoto et al. |
| 2008/0039255 A1* | 2/2008 | Jinno .................. A61B 17/062 474/148 |
| 2008/0249551 A1 | 10/2008 | Sunaoshi et al. |
| 2009/0030428 A1 | 1/2009 | Omori et al. |
| 2009/0030449 A1 | 1/2009 | Kawai et al. |
| 2009/0031842 A1 | 2/2009 | Kawai et al. |
| 2009/0036901 A1 | 2/2009 | Omori |
| 2009/0062814 A1 | 3/2009 | Omori et al. |
| 2009/0163948 A1* | 6/2009 | Sunaoshi ............... A61B 34/70 606/205 |
| 2009/0216248 A1* | 8/2009 | Uenohara ............. A61B 17/29 606/130 |
| 2010/0048997 A1 | 2/2010 | Okada |
| 2010/0076483 A1 | 3/2010 | Imuta |
| 2010/0079099 A1 | 4/2010 | Katsuki et al. |
| 2010/0082041 A1 | 4/2010 | Prisco |
| 2010/0170519 A1 | 7/2010 | Romo et al. |
| 2010/0175701 A1* | 7/2010 | Reis ...................... A61B 46/23 128/852 |
| 2010/0331820 A1 | 12/2010 | Prisco et al. |
| 2011/0144656 A1 | 6/2011 | Lee et al. |
| 2011/0146441 A1 | 6/2011 | Graham et al. |
| 2011/0282491 A1 | 11/2011 | Prisco et al. |
| 2011/0290855 A1* | 12/2011 | Moore .................. A61B 17/072 227/180.1 |
| 2012/0059360 A1 | 3/2012 | Namiki |
| 2012/0143211 A1 | 6/2012 | Kishi |
| 2012/0298719 A1 | 11/2012 | Shelton, IV et al. |
| 2013/0023860 A1* | 1/2013 | Nagashimada ........ A61B 34/70 606/1 |
| 2013/0110129 A1 | 5/2013 | Reid et al. |
| 2013/0150673 A1* | 6/2013 | Kakehashi ........... A61B 1/0052 600/142 |
| 2013/0255410 A1 | 10/2013 | Lee et al. |
| 2014/0000411 A1* | 1/2014 | Shelton, IV ........... A61B 34/30 74/650 |
| 2014/0001234 A1* | 1/2014 | Shelton, IV ..... A61B 17/07207 227/176.1 |
| 2014/0001235 A1* | 1/2014 | Shelton, IV ..... A61B 17/07207 227/176.1 |
| 2014/0001236 A1* | 1/2014 | Shelton, IV ..... A61B 17/07207 227/176.1 |
| 2014/0005654 A1* | 1/2014 | Batross ............. A61B 17/32009 606/33 |
| 2014/0005667 A1 | 1/2014 | Stulen et al. |
| 2014/0005678 A1* | 1/2014 | Shelton, IV ..... A61B 17/07207 606/130 |
| 2014/0005681 A1 | 1/2014 | Gee et al. |
| 2014/0012287 A1* | 1/2014 | Oyola .................... A61B 90/50 606/130 |
| 2014/0114327 A1* | 4/2014 | Boudreaux ........... A61B 34/25 606/130 |
| 2014/0114334 A1 | 4/2014 | Olson et al. |
| 2014/0276950 A1 | 9/2014 | Smaby et al. |
| 2014/0276951 A1 | 9/2014 | Hourtash et al. |
| 2014/0299648 A1* | 10/2014 | Shelton, IV ......... A61B 17/105 227/180.1 |
| 2014/0316432 A1* | 10/2014 | Malkowski ....... A61B 17/00234 606/130 |
| 2015/0313619 A1* | 11/2015 | Tadano ................. A61B 34/71 606/130 |
| 2016/0074121 A1 | 3/2016 | Yorimoto et al. |
| 2016/0287346 A1 | 10/2016 | Hyodo et al. |
| 2016/0310221 A1* | 10/2016 | Bar ..................... A61B 34/30 |
| 2017/0296184 A1* | 10/2017 | Harris ................ A61B 17/072 |

FOREIGN PATENT DOCUMENTS

| | | |
|---|---|---|
| EP | 1 915 967 A1 | 4/2008 |
| EP | 2 095 778 A1 | 9/2009 |
| JP | 2004-105451 A | 4/2004 |
| JP | 2004-122286 A | 4/2004 |
| JP | 2008-104854 A | 5/2008 |
| JP | 2008-104855 A | 5/2008 |
| JP | 2008-253464 A | 10/2008 |
| JP | 2008-284214 A | 11/2008 |
| JP | 2009-028156 A | 2/2009 |
| JP | 2009-028157 A | 2/2009 |
| JP | 2009-028425 A | 2/2009 |
| JP | 2009-045428 A | 3/2009 |
| JP | 2009-056164 A | 3/2009 |
| JP | 2009-148859 A | 7/2009 |
| JP | 2009-213540 A | 9/2009 |
| JP | 2009-213653 A | 9/2009 |
| JP | 2009-226028 A | 10/2009 |
| JP | 2009-226029 A | 10/2009 |
| JP | 2009-226093 A | 10/2009 |
| JP | 2009-226194 A | 10/2009 |
| JP | 2010-022414 A | 2/2010 |
| JP | 2010-022415 A | 2/2010 |
| JP | 2010-022416 A | 2/2010 |
| JP | 2010-035875 A | 2/2010 |
| JP | 2010-038793 A | 2/2010 |
| JP | 2010-046384 A | 3/2010 |
| JP | 2010-051497 A | 3/2010 |
| JP | 2010-075242 A | 4/2010 |
| JP | 2010-082309 A | 4/2010 |
| JP | 2010-220955 A | 10/2010 |
| JP | 2010-227600 A | 10/2010 |
| JP | 2010-268844 A | 12/2010 |
| JP | 2012-504016 A | 2/2012 |
| JP | 2012-055377 A | 3/2012 |
| JP | 2012-115553 A | 6/2012 |
| JP | 2012-120884 A | 6/2012 |
| JP | 2012-531943 A | 12/2012 |
| JP | 2013-510664 A | 3/2013 |
| JP | 2013-528066 A | 7/2013 |
| JP | 2014-079653 A | 5/2014 |
| JP | 2014-512845 A | 5/2014 |
| JP | 2014-193417 A | 10/2014 |
| WO | 2007/075864 A1 | 7/2007 |
| WO | 2011/060054 A2 | 5/2011 |

(56) References Cited

FOREIGN PATENT DOCUMENTS

| WO | 2011/108840 A2 | 9/2011 |
| WO | 2011/122516 A1 | 10/2011 |
| WO | 2012/068156 A2 | 5/2012 |
| WO | 2012/166468 A1 | 12/2012 |
| WO | 2012/166470 A1 | 12/2012 |
| WO | 2012/166476 A1 | 12/2012 |
| WO | 2012/166503 A1 | 12/2012 |
| WO | 2012/166517 A1 | 12/2012 |
| WO | 2014/069003 A1 | 5/2014 |
| WO | 2014/157001 A1 | 10/2014 |
| WO | 2015/093602 A1 | 6/2015 |

\* cited by examiner

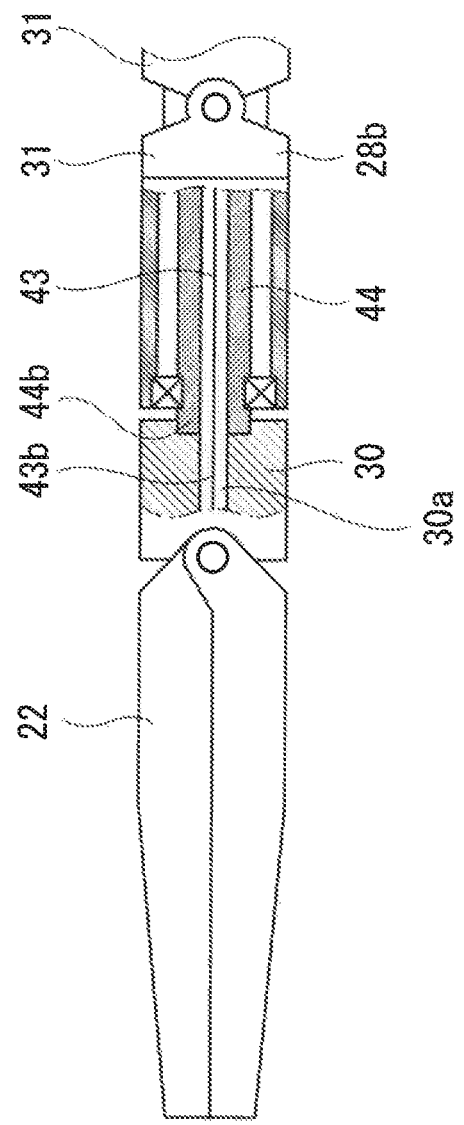

SURGICAL ROBOT

TECHNICAL FIELD

The present invention relates to a surgical robot.

BACKGROUND ART

A manipulator system capable of being used in minimally invasive surgery and including a manipulator detachable from a manipulator main body has been known (see PTL 1, for example).

The manipulator system includes the manipulator attachable to the manipulator main body through an arm. The manipulator includes: a holding portion (surgical tool) holding suture thread, a needle, etc.; a tip end portion; an intermediate portion forming a second joint together with the tip end portion; and a root portion including a tubular portion and forming a first joint together with the intermediate portion. The arm includes a mechanism configured to rotate the tubular portion around an axis of the tubular portion. By rotating the tubular portion around the axis of the tubular portion, the holding portion can be rotated around the axis of the tubular portion.

CITATION LIST

Patent Literature

PTL 1: Japanese Laid-Open Patent Application Publication No. 2004-122286

SUMMARY OF INVENTION

Technical Problem

For example, when performing an operation of bolding the suture thread by the holding portion, an opening/closing direction of the holding portion needs to coincide with a direction perpendicular to an extending direction of the suture thread. Therefore, an angular position of the holding portion around an axis of the holding portion needs to be adjusted. According to the manipulator system described in PTL 1, to change the opening/closing direction of the holding portion, the entire manipulator needs to be rotated around the axis of the tubular portion. Thus, there is a problem that when the axis of the tubular portion and the axis of the holding portion do not coincide with each other, such as especially when the first joint and the second joint are in a bent state, the holding portion largely moves in a circumferential direction about the axis of the tubular portion, and therefore, operability is low.

Solution to Problem

To solve the above problem, a surgical robot according to one aspect of the present invention includes: a robot main body driving mechanism including a wrist joint driving portion; and a robot main body including a base detachably fixed to the robot main body driving mechanism, an arm including a hollow shaft and a wrist joint, the shaft including a proximal end continuous with the base, the wrist joint being continuous with a distal end of the shaft, the wrist joint rotating around an axis of a distal end of the arm, an end effector attached to the wrist joint, and a wrist joint driving force transmission portion including a hollow torque transmission tube, the torque transmission tube being inserted through the shaft and including a distal end attached to the wrist joint, wherein: by attaching the base to the robot main body driving mechanism, the wrist joint driving portion is connected to a proximal end of the torque transmission tube to rotate the torque transmission tube around an axis of the torque transmission tube; and by detaching the base from the robot main body driving mechanism, the wrist joint driving portion is separated from the torque transmission tube.

According to this configuration, the base can be detached from the robot main body driving mechanism, and thus, the driving force transmission mechanism and the robot main body driving mechanism can be separated from each other. Therefore, the robot main body that contacts a patient can be detached from the robot main body driving mechanism, and the robot main body can be subjected to a sterilization treatment. On this account, the sterilization treatment of the surgical robot can be efficiently performed.

Further, by attaching the base to the robot main body driving mechanism, the wrist joint driving portion can be connected to the proximal end of the torque transmission tube and can rotate the torque transmission tube around the axis of the torque transmission tube. With this, the end effector provided at the distal end of the arm can be rotated around the axis of the distal end of the arm. Therefore, even when the arm is in a bent state, an angular position of the end effector around the axis of the distal end of the arm can be changed. Thus, operability of the surgical robot can be improved.

The shaft and the torque transmission tube may have flexibility.

According to this configuration, the shaft and the torque transmission tube can be curved to bypass an organ and the like of the patient, and thus, the end effector can be introduced to the vicinity of the treated part. Further, the wrist joint can be rotated accurately.

The surgical robot may be configured such that: the robot main body driving mechanism includes an end effector driving portion; the robot main body includes an end effector driving force transmission portion; the end elector driving force transmission portion includes an end effector operating cable and an end effector operating cable pulling pulley; the end effector operating cable is inserted through the torque transmission tube and includes a distal end attached to the end effector; the end effector operating cable pulling pulley rotates to move the end effector operating cable in an extending direction of the end effector operating cable; the end effector is operated by the movement of the end effector operating cable in the extending direction of the end effector operating cable; by attaching the base to the robot main body driving mechanism, the end effector driving portion is connected to the end effector operating cable pulling pulley to rotate the end effector operating cable pulling pulley; and by detaching the base from the robot main body driving mechanism, the end effector driving portion is separated from the end effector operating cable pulling pulley.

According to this configuration, it is possible to prevent a case where by bending the shaft, the end effector operating cable is moved, and this operates the end effector.

The surgical robot may be configured such that: the wrist joint driving portion includes a driving-side wrist joint driving rotating body rotated by rotation of a driving shaft of the wrist joint driving portion; the end effector driving portion includes a driving-side end effector driving rotating body rotated by rotation of a driving shaft of the end effector driving portion; the wrist joint driving force transmission portion includes a hollow coupling portion fixed to the proximal end of the torque transmission tube and supported by the base so as to be rotatable around an axis of the proximal end of the torque transmission tube, the coupling portion including an internal space communicating with an internal space of the torque transmission tube and a driven-side wrist joint driving rotating body fixed to the coupling portion and including a through hole extending on the axis of the proximal end of the torque transmission tube, the driven-side wrist joint driving rotating body being connected to the driving-side wrist joint driving rotating body by attaching the base to the robot main body driving mechanism; and the end effector driving force transmission portion includes the end effector operating cable pulling pulley provided in the internal space of the coupling portion, a rotating shaft fixed to the end effector operating cable pulling pulley and supported by the base so as to be rotatable around the axis of the proximal end of the torque transmission tube, the rotating shaft being inserted through the through hole of the driven-side wrist joint driving rotating body, and a driven-side end effector driving rotating body fixed to the rotating shaft, the driven-side end effector driving rotating body being connected to the driving-side end effector driving rotating body by attaching the base to the robot main body driving mechanism.

According to this configuration, by rotating the driven-side forceps driving rotating body and the driven-side wrist joint driving rotating body at the same time, the angular position of the end effector around the axis of the distal end of the arm can be changed without operating the end effector.

Further, since the driving-side forceps driving rotating body and the driven-side wrist joint driving rotating body are provided on the same axis, the base can be reduced in size.

The surgical robot may be configured such that: the robot main body driving mechanism includes a bending joint driving portion; the arm includes a bending joint provided between the shaft and the wrist joint and configured to perform a bending operation of bending the arm; the robot main body includes a bending joint driving force transmission portion; the bending joint driving force transmission portion includes a bending joint operating cable and a bending joint operating cable pulling pulley; the bending joint operating cable includes a distal end attached to the bending joint; the bending joint operating cable pulling pulley rotates to move the bending joint operating cable in an extending direction of the bending joint operating cable; the bending joint performs the bending operation by the movement of the bending joint operating cable in the extending direction of the bending joint operating cable; by attaching the base to the robot main body driving mechanism, the bending joint driving portion is connected to the bending joint operating cable pulling pulley to rotate the bending joint operating cable pulling pulley; and by detaching the base from the robot main body driving mechanism, the bending joint operating cable pulling pulley and the wrist joint driving portion are separated from each other.

According to this configuration, the arm of the end effector can be bent, and the operability of the surgical robot can be improved.

The bending joint operating cable may be inserted through a space between the shaft and the torque transmission tube.

According to this configuration, the bending joint can be operated independently from the operation of the end effector and the operation of the wrist joint.

The end effector may be a pair of forceps.

According to this configuration, the surgical robot is applicable to work of holding a target.

Advantageous Effects of Invention

The present invention has an effect of being able to improve the operability of the surgical robot.

BRIEF DESCRIPTION OF DRAWINGS

FIG. 7 is a partial breakaway view showing a configuration example of a wrist joint of the robot main body of the surgical robot of FIG. 1.

DESCRIPTION OF EMBODIMENTS

Hereinafter, an embodiment of the present invention will be explained in reference to the drawings. It should be noted that the present invention is not limited by the present embodiment. In the following explanations and the drawings, the same reference signs are used for the same or corresponding components, and a repetition of the same explanation is avoided.

Figure 1:
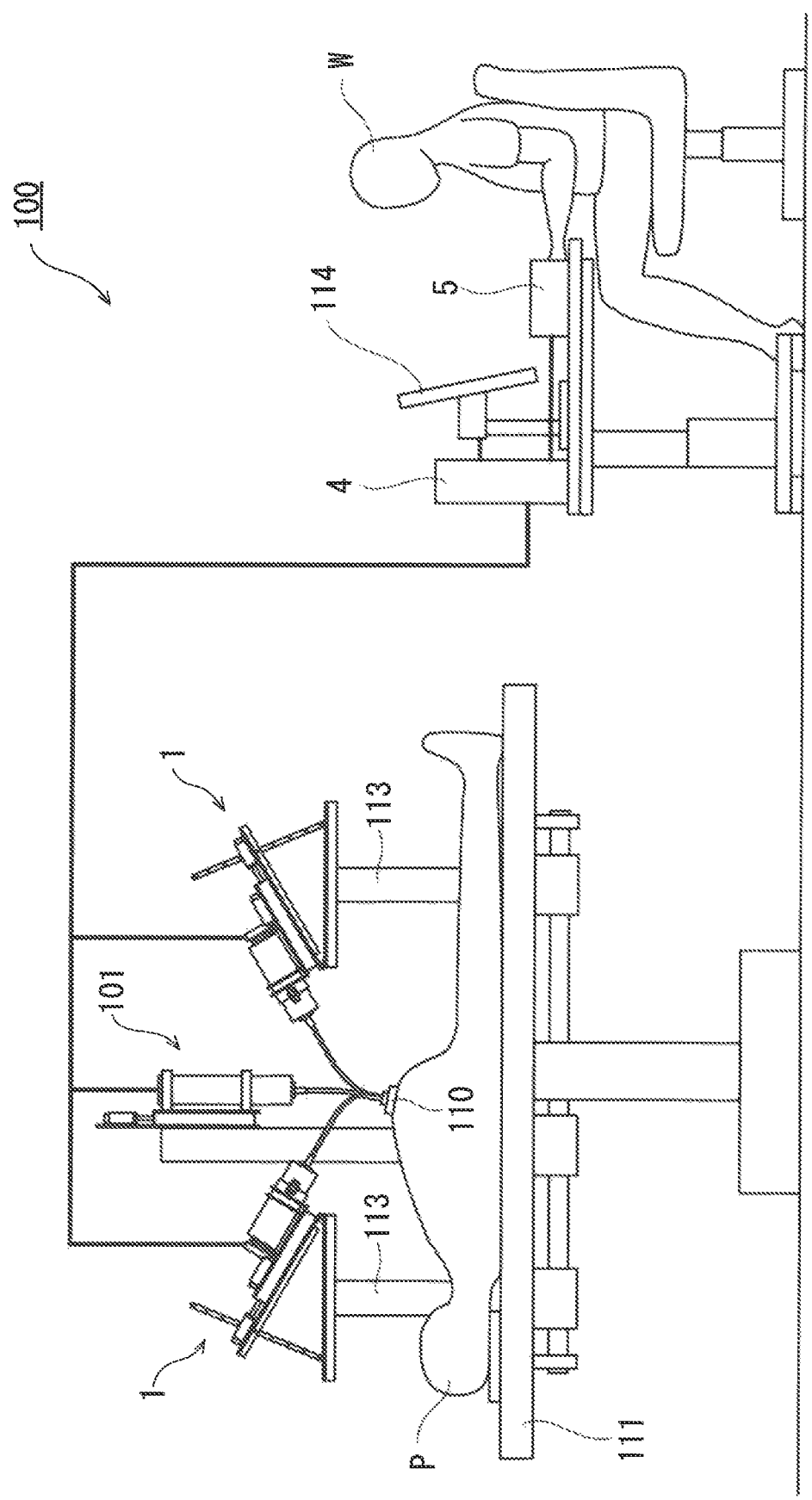
FIG. 1 is a diagram schematically showing a configuration example of a surgical robot system including a surgical robot according to an embodiment of the present invention.
Figure 2:
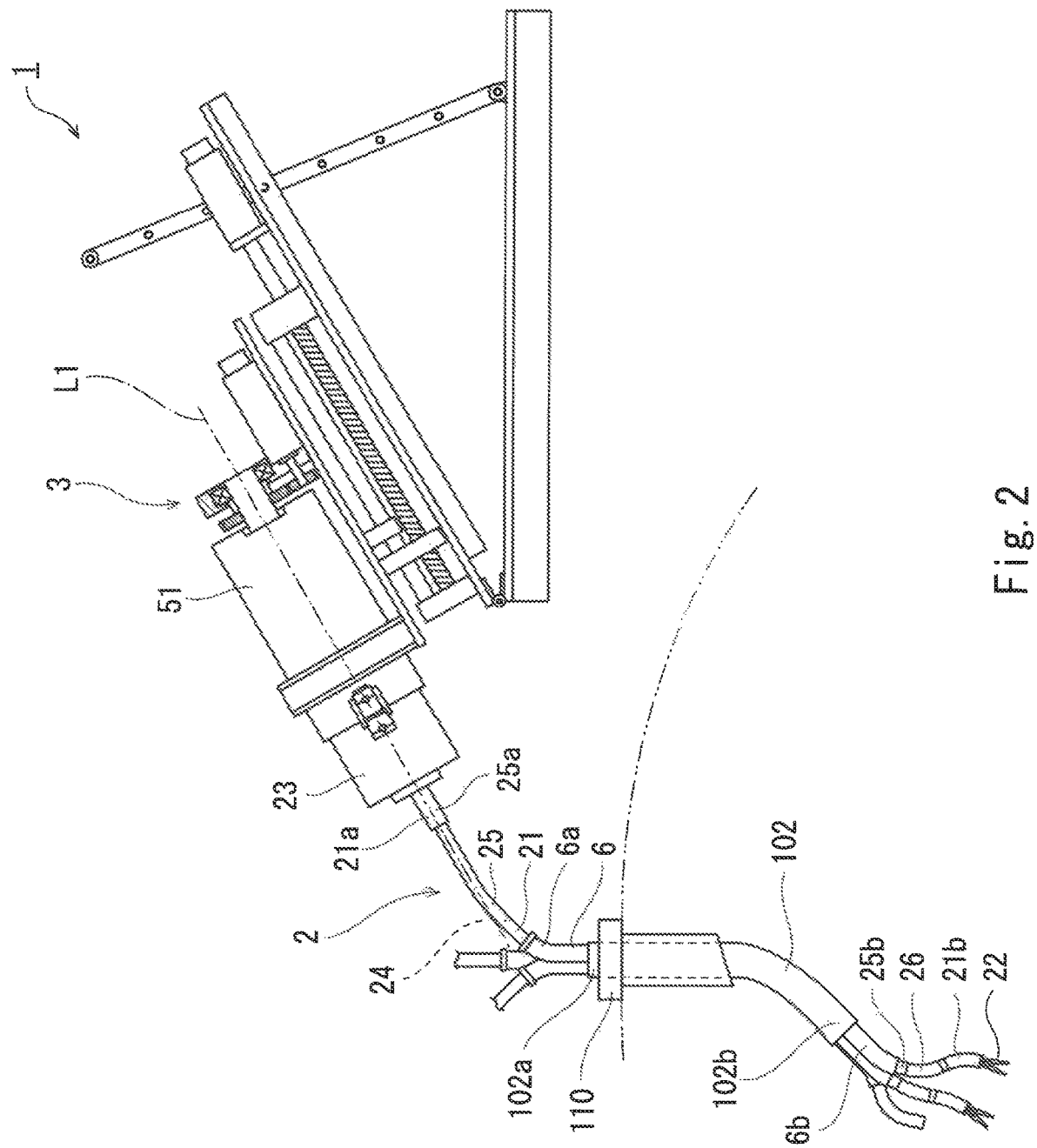
FIG. 2 is a diagram showing a configuration example of the surgical robot of FIG. 1.

FIG. 1 is a diagram schematically showing a configuration example of a surgical robot system 100 including a surgical robot 1 according to the embodiment of the present invention. FIG. 2 is a diagram showing a configuration example of the surgical robot 1.

As shown in FIG. 1, the surgical robot system 100 is a system used when an operator W remotely operates a surgical tool from an outside to perform minimally invasive surgery, the surgical tool being provided at a distal end of the surgical robot 1 and inserted into a body of a patient P on an operating table 111.

For example, the surgical robot system 100 includes one or more surgical robots 1 and an endoscope 101.

The surgical robot 1 is supported by a surgical robot support base 113 attached to the operating table 111. The surgical robot 1 includes an arm formed in a thin and long shape and further includes a surgical tool at a distal end of the arm. A treated part in the body of the patient P is treated by the surgical tool. In the present embodiment, the surgical robot 1 is a robot including a pair of forceps at the distal end of the arm. However the surgical tool at the distal end of the arm is not limited to the forceps, and various surgical tools are applicable.

The endoscope 101 is used by the operator W to visually recognize the inside of the body of the patient P and includes a video camera and a light at a distal end of the endoscope 101. An image taken by the video camera of the endoscope 101 is displayed on a display device 114. With this, the operator W can operate the surgical robot 1 to perform surgery while visually recognizing states of the distal end of the arm and the surgical tool in the body of the patient P and a state of the treated part.

As shown in FIG. 2, the surgical robots 1 are inserted into a collectively bundling pipe 102 to be collectively bundled. The collectively bundling pipe 102 has flexibility and is formed in a hollow tubular shape.

Configuration Example of Robot Main Body

Figure 3:
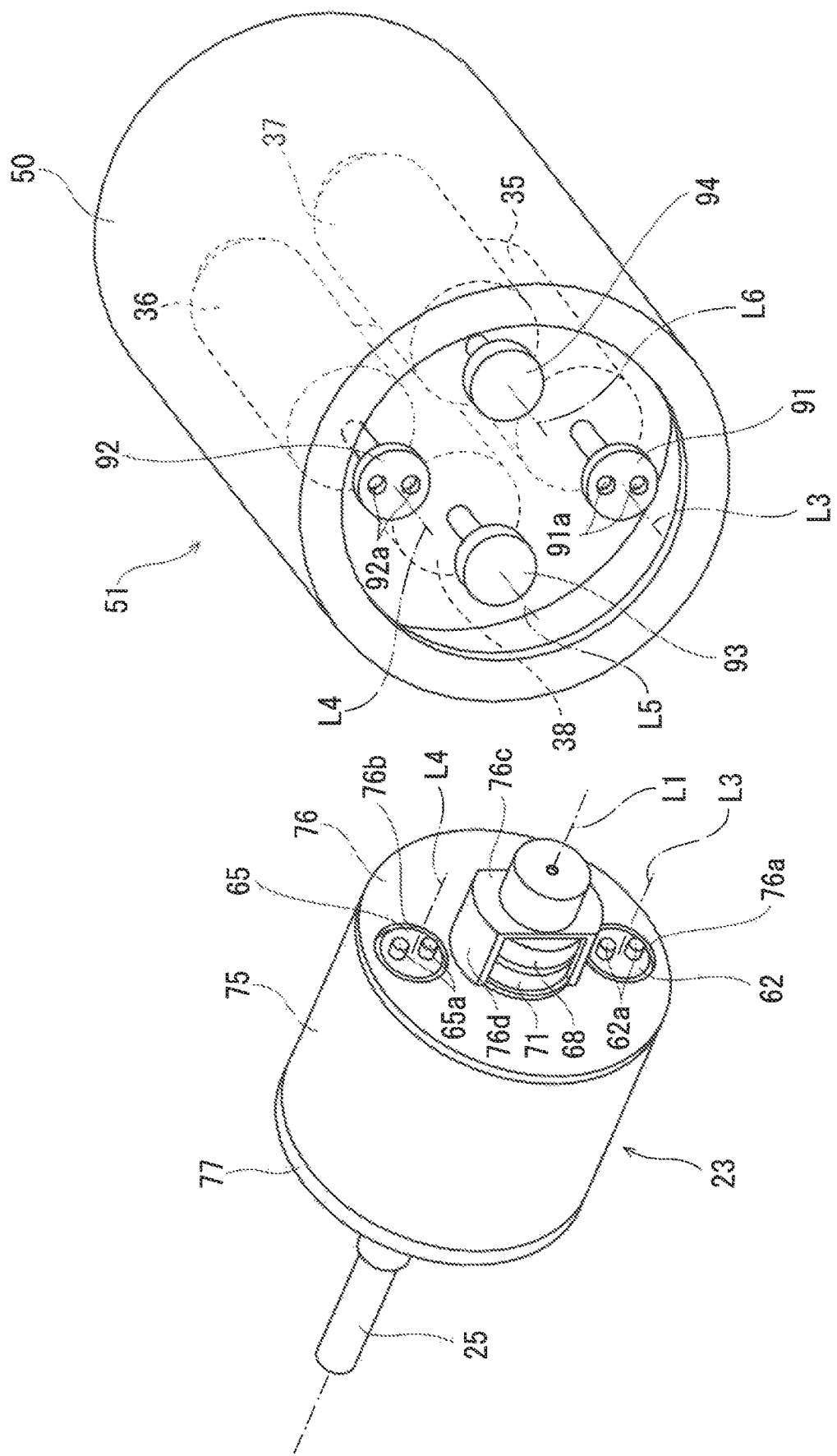
FIG. 3 is a perspective view showing configuration examples of a proximal end of the robot main body of the surgical robot of FIG. 1 and a robot main body driving mechanism.
Figure 4:
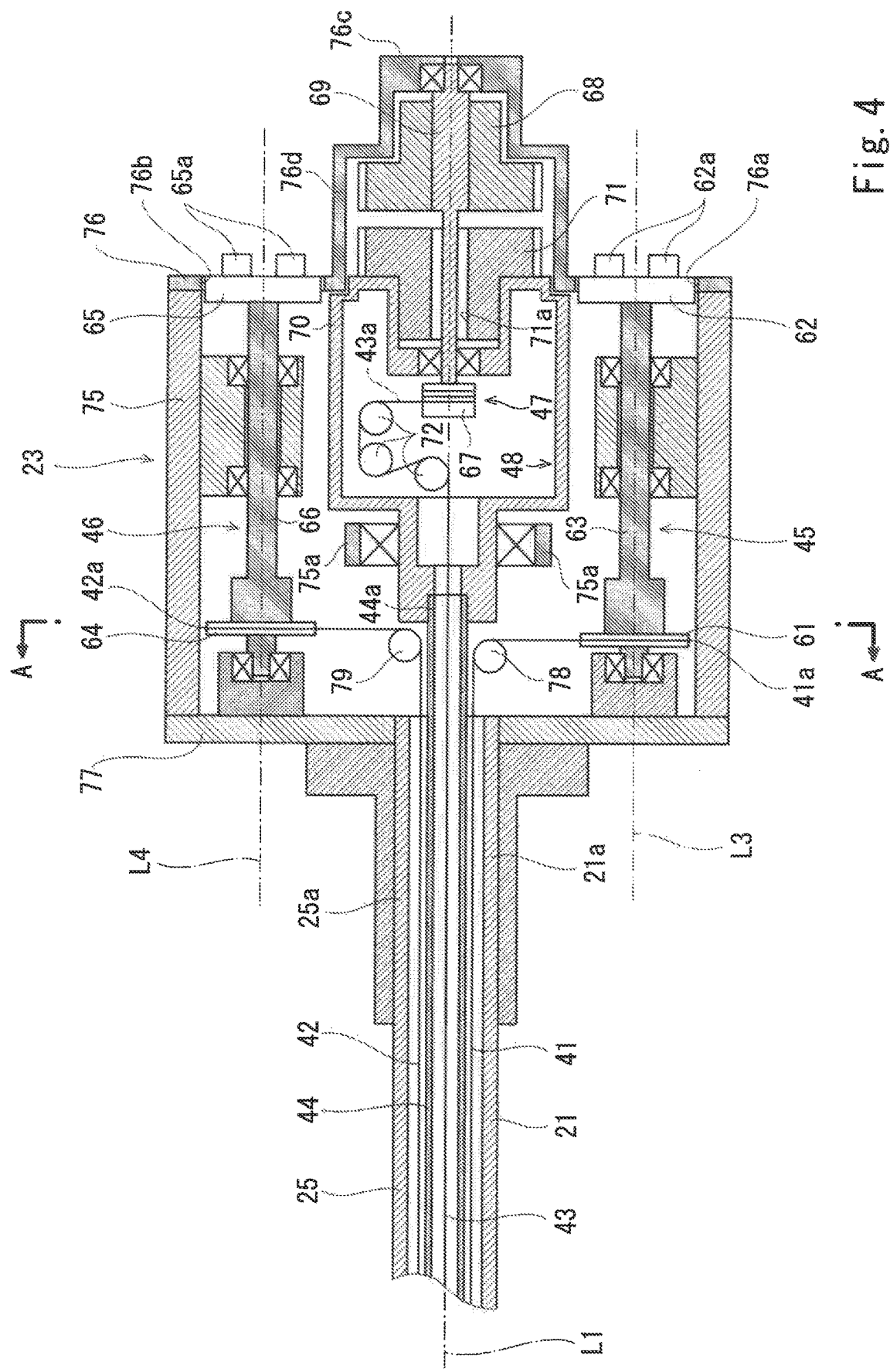
FIG. 4 is a sectional view showing a configuration example of the proximal end of the robot main body of the surgical robot of FIG. 1.
Figure 5:
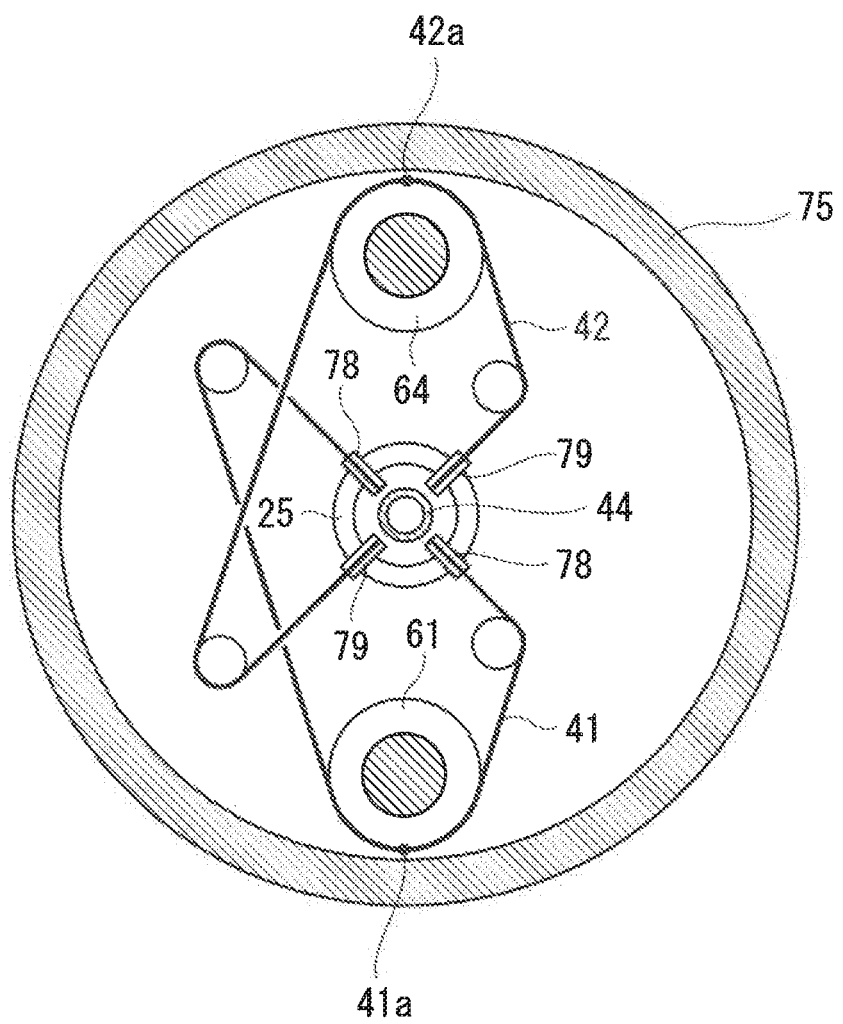
FIG. 5 is an A-A arrow view showing a configuration example of the proximal end of the robot main body of the surgical robot of FIG. 1.

FIG. 3 is a perspective view showing configuration examples of a proximal end of the robot main body 2 and a robot main body driving mechanism 51. FIG. 4 is a sectional view showing a configuration example of the proximal end of the robot main body 2. FIG. 5 is an A-A arrow view showing a configuration example of the proximal end of the robot main body 2.

As shown in FIG. 2, the surgical robot 1 includes the robot main body 2, a driving portion 3, a control unit 4 (see FIG. 1), and an operating portion 5 (see FIG. 1). Further, in the present embodiment, the surgical robot 1 includes a guide pipe 6.

The robot main body 2 includes: a base 23; an arm 21 including a proximal end 21a continuous with the base 23; an end effector (forceps) 22 provided at a distal end 21b of the arm 21; and a driving force transmission mechanism 24. It should be noted that the term "continuous" denotes not only a case where two members are directly connected to each other but also a case where two members are indirectly connected to each other with another member interposed therebetween.

The base 23 is detachably fixed to the below-described robot main body driving mechanism 51 of the driving portion 3. With this, the robot main body 2 can be coupled to the driving portion 3. As shown in FIGS. 3 and 4, the base 23 includes: a tubular portion 75 formed in a tubular shape; a driving portion-side end plate 76 attached to a peripheral edge of the tubular portion 75 which edge is located close to the robot main body driving mechanism 51 (driving portion 3) with the base 23 attached to the robot main body driving mechanism 51; and an arm-side end plate 77 attached to a peripheral edge of the tubular portion 75 which edge is located close to the arm 21.

The tubular portion 75 is continuous with the arm 21 so as to extend in a direction along an axis L1 of a proximal end 44a of a below-described torque transmission tube 44 of the arm 21. As shown in FIG. 4, a supporting portion 75a is provided in the tubular portion 75. The supporting portion 75a is a rod-shaped body extending in a near-side direction and a depth direction in FIG. 4, and both end portions of the supporting portion 75a are fixed to an inner peripheral surface of the tubular portion 75. The supporting portion 75a supports one of end portions of a below-described coupling portion 70.

The driving portion-side end plate 76 includes a first through hole 76a connecting outer and inner surfaces of the driving portion-side end plate 76. The first through hole 76a is formed on a below-described axis L3. A below-described driven-side first bending joint driving rotating body 62 is provided in the first through hole 76a. The driving portion-side end plate 76 includes a second through hole 76b connecting the outer and inner surfaces of the driving portion-side end plate 76. The second through hole 76b is formed on a below-described axis L4. A below-described driven-side second bending joint driving rotating body 65 is provided in the second through hole 76b. The second through hole 76b is formed at a position where the first through hole 76a reaches by being rotated about the axis L1 by about 180 degrees.

The driving portion-side end plate 76 includes a hollow projecting portion 76c projecting toward the robot main body driving mechanism 51 with the base 23 attached to the robot main body driving mechanism 51. The projecting portion 76c is formed on the axis L1. To be specific, the projecting portion 76c is located between the first through hole 76a and the second through hole 76b. The projecting portion 76c includes a peripheral wall 76d extending in a circumferential direction about the axis L1. An internal space of the peripheral wall 76d communicates with an internal space of the tubular portion 75. A below-described driven-side end effector driving rotating body 68 and a below-described driven-side wrist joint driving rotating body 71 are provided in the internal space of the peripheral wall 76d. A part of the peripheral wall 76d which part is located between a position where the first through hole 76a reaches by being rotated about the axis L1 by about 90 degrees and a group of the below-described driven-side end effector driving rotating body 68 and the below-described driven-side wrist joint driving rotating body 71 is removed, and teeth of the driven-side end effector driving rotating body 68 and teeth of the driven-side wrist joint driving rotating body 71 are exposed therefrom. Further, a part of the peripheral wall 76d which part is located between a position where the second through hole 76b reaches by being rotated about the axis L1 by about 90 degrees and the group of the below-described driven-side end effector driving rotating body 68 and the driven-side wrist joint driving rotating body 71 is removed, and the teeth of the driven-side end effector driving rotating body 68 and the teeth of the driven-side wrist joint driving rotating body 71 are exposed therefrom.

Further, as shown in FIGS. 4 and 5, the base 23 includes a pair of first bending joint operating cable direction changing pulleys 78 and a pair of second bending joint operating cable direction changing pulleys 79, and the pulleys 78 and 79 are attached to the inner peripheral surface of the tubular portion 75. The pair of first bending joint operating cable direction changing pulleys 78 are pulleys for changing an extending direction of a below-described first bending joint operating cable 41. The pair of second bending joint operating cable direction changing pulleys 79 are pulleys for changing an extending direction of a below-described second bending joint operating cable 42.

The first bending joint operating cable direction changing pulleys 78 and the second bending joint operating cable direction changing pulleys 79 are arranged such that the positions of the pulleys 78 are different in a direction along the axis L1 from the positions of the pulleys 79. To be specific, in the present embodiment, the first bending joint operating cable direction changing pulleys 78 are located closer to the arm 21 than the second bending joint operating cable direction changing pulleys 79 (i.e., located at a left side on the paper surface of FIG. 4).

Figure 6A:
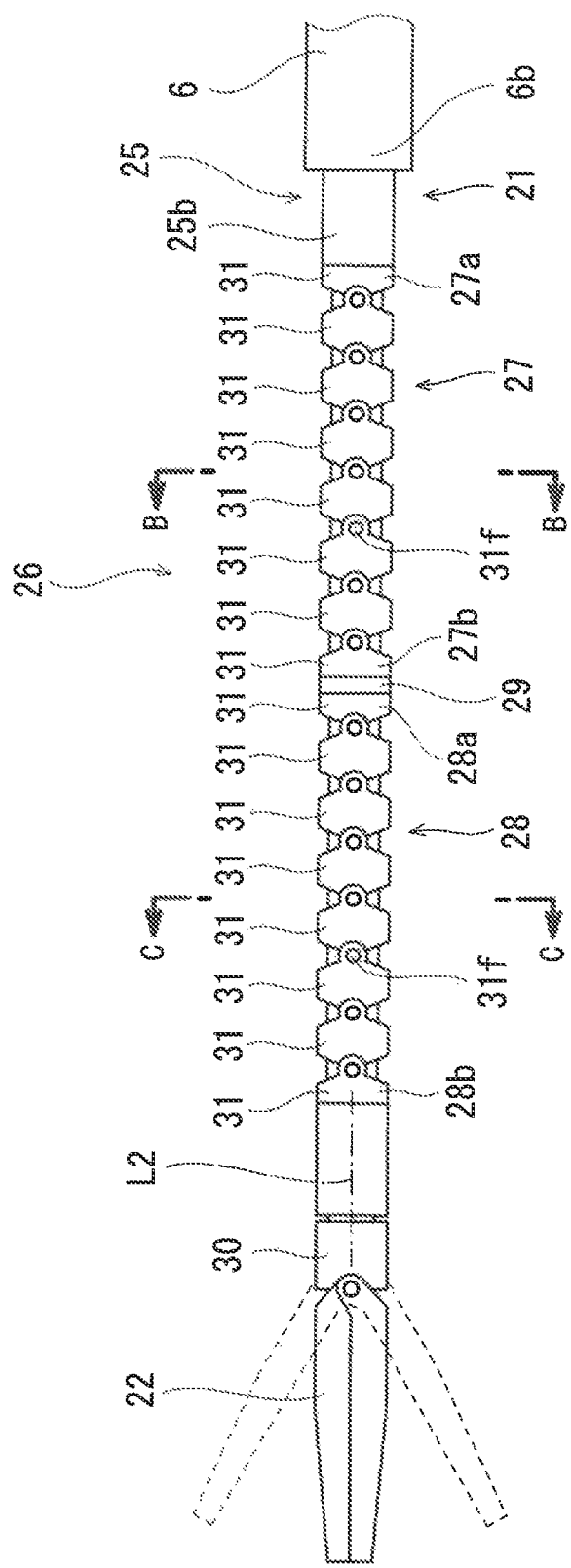
FIG. 6A is a diagram showing a configuration example of a distal end of a robot main body of the surgical robot of FIG. 1 and is a diagram showing a state where a joint portion of the robot main body is linearly stretched.
Figure 6B:
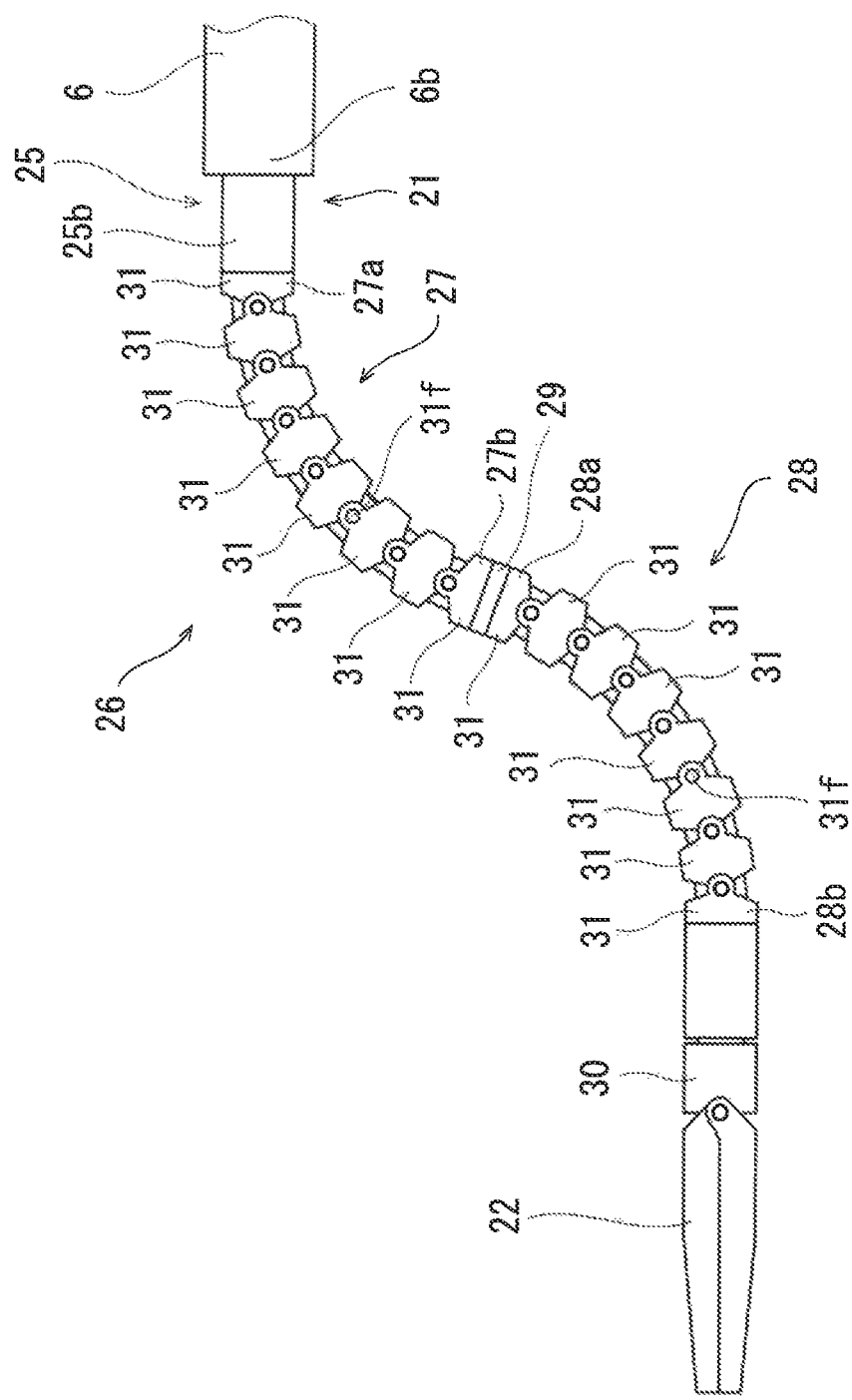
FIG. 6B is a diagram showing a configuration example of the distal end of the robot main body of the surgical robot of FIG. 1 and is a diagram showing a state where the joint portion of the robot main body is bent.

FIG. 6A is a diagram showing a configuration example of a distal end of the robot main body 2 and is a diagram showing a state where a joint portion 26 is linearly stretched. FIG. 6B is a diagram showing a configuration example of the distal end of the robot main body 2 and is a diagram showing a state where the joint portion 26 is bent.

As shown in FIGS. 4, 5, 6A, and 6B, the arm 21 includes a hollow flexible shaft (shaft) 25 and the joint portion 26.

The flexible shaft 25 is, for example, a tubular body having flexibility. As shown in FIG. 4, a proximal end 25a of the flexible shall 25 is attached and fixed to the arm-side end plate 77 of the base 23. To be specific, the proximal end 25a of the flexible shaft 25 is continuous with the base 23. An internal space of the flexible shaft 25 communicates with an internal space of the base 23.

As shown in FIGS. 6A and 6B, a proximal end of the joint portion 26 (i.e., a proximal end 27a of a first bending joint 27) is continuous with a distal end 25b of the flexible shaft 25. The joint portion 26 is a hollow tubular body, and an internal space of the joint portion 26 communicates with the internal space of the flexible shaft 25.

In the present embodiment, the joint portion 26 includes the first bending joint 27, a second bending joint 28, a connecting portion 29, and a wrist joint 30. The first bending joint 27, the second bending joint 28, the connecting portion 29, and the wrist joint 30 are arranged on the same axis. An outer peripheral surface of the joint portion 26 is covered with a cover (not shown), and the joint portion 26 is substantially the same in diameter as the flexible shaft 25.

The first bending joint 27 is a hollow tubular body, and the proximal end 27a thereof is attached to the distal end 25b of the flexible shaft 25 so as to be continuous with the distal end 25b.

Figure 9A:
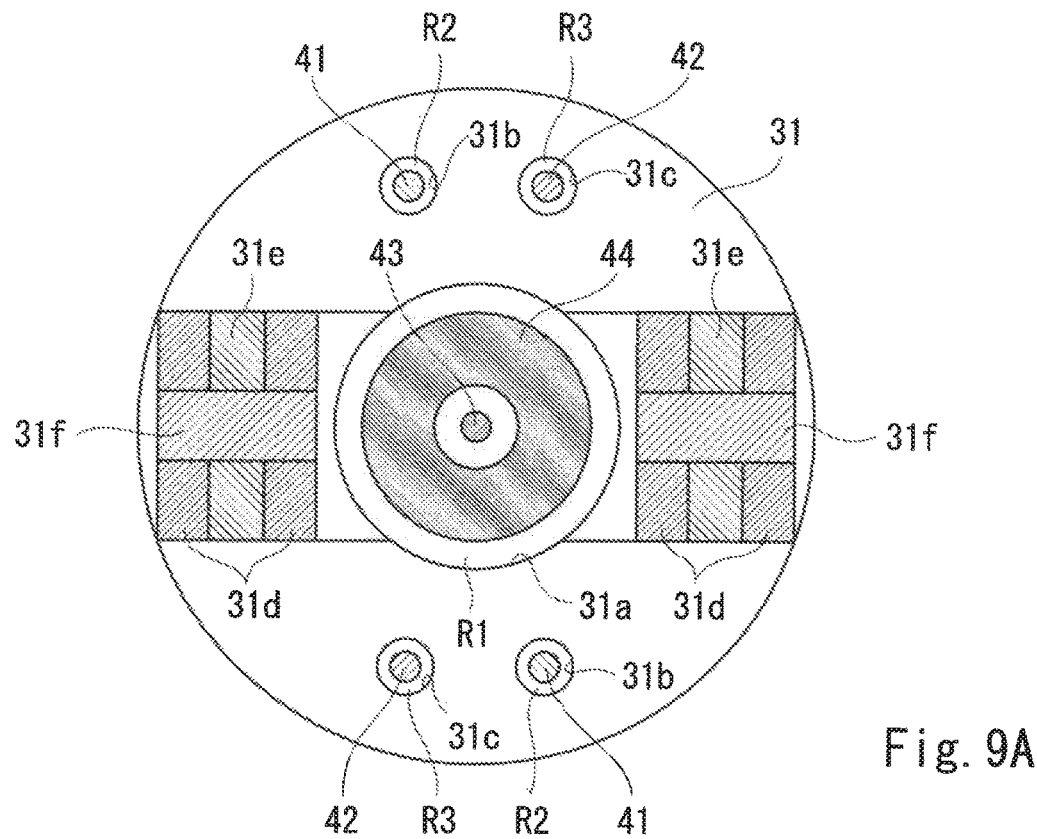
FIG. 9A is a B-B arrow view showing a configuration example of the distal end of the robot main body of the surgical robot of FIG. 1.
Figure 9B:
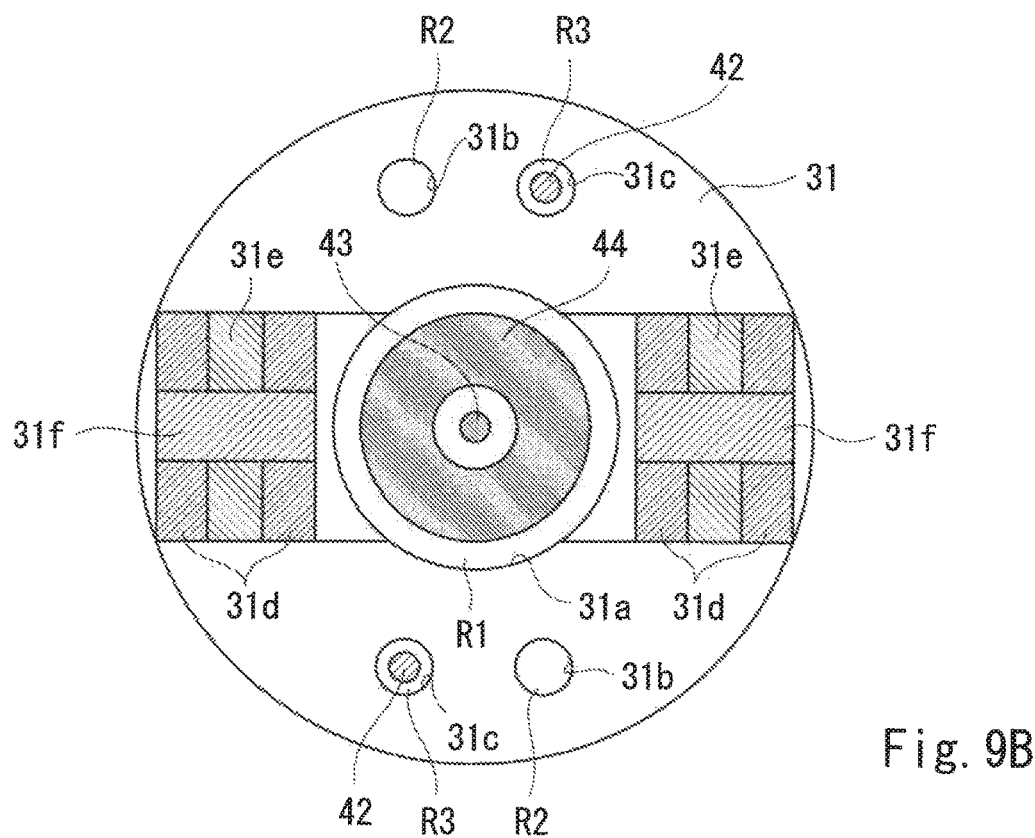
FIG. 9B is a C-C arrow view showing a configuration example of the distal end of the robot main body of the surgical robot of FIG. 1.

FIG. 9A is a B-B arrow view showing a configuration example of the distal end of the robot main body 2. FIG. 9B is a C-C arrow view showing a configuration example of the distal end of the robot main body 2.

The first bending joint 27 includes a plurality of frame members 31 that are continuous in a row in an axial direction of the joint portion 26. Each of the frame members 31 is formed in a columnar shape extending in the axial direction of the joint portion 26. The frame member 31 is formed in such a tapered shape that when viewed from a direction perpendicular to an axis of the frame member 31 and a bending direction of the below-described first bending joint 27 (i.e., when viewed from an extending direction of a below-described pin 31f), a thickness of the frame member 31 in an axial direction decreases as the frame member 31 extends away from the axis of the frame member 31. To be specific, the frame member 31 is formed so as to be thinner as it extends upward and downward in FIG. 6A. With this, interference between opposing end surfaces of the adjacent frame members 31 when the first bending joint 27 is bent is avoided.

As shown in FIGS. 9A and 9B, the frame member 31 includes a first insertion hole 31a, a pair of second insertion holes 31b, and a pair of third insertion holes 31c.

The first insertion hole 31a is formed on the axis of the frame member 31, and the below-described torque transmission tube 44 is inserted through the first insertion hole 31a. The first insertion holes 31a of the plurality of frame members 31 that are continuous in a row constitute a first route R1 extending in an extending direction of the arm 21.

The pair of second insertion holes 31b connect both end surfaces of the frame member 31 and extend parallel to the axis of the frame member 31. When viewed from the direction perpendicular to the axis of the frame member 31 and the bending direction of the below-described first bending joint 27 (i.e., when viewed from the extending direction of the below-described pin 31f), one of the pair of second insertion holes 31b is located at an opposite side of the other of the pair of second insertion holes 31b across the axis of the frame member 31. To be specific, in FIG. 6A, one of the pair of second insertion holes 31b is formed above the below-described pin 31f, and the other is formed under the below-described pin 31f. Both end portions of the below-described first bending joint operating cable 41 are inserted through the respective second insertion holes 31b. The pairs of second insertion holes 31b of the plurality of frame members 31 that are continuous in a row constitute a pair of second routes R2 extending in the extending direction of the arm 21. Therefore, when viewed from the extending direction of the below-described pin 31f, one of the pair of second routes R2 is located at an opposite side of the other of the pair of second routes R2 across the axis of the frame member 31.

The pair of third insertion holes 31c connect both end surfaces of the fame member 31 and extend parallel to the axis of the frame member 31. When viewed from the direction perpendicular to the axis of the frame member 31 and the bending direction of the below-described first bending joint 27, one of the pair of third insertion holes 31c is located at an opposite side of the other of the pair of third insertion holes 31c across the axis of the frame member 31. To be specific, in FIG. 6A, one of the pair of third insertion holes 31c is formed above the below-described pin 31f, and the other is formed under the below-described pin 31f. Both end portions of a below-described second bending joint operating cable 42 are inserted through the respective third insertion holes 31c. The pairs of third insertion holes 31c of the plurality of frame members 31 that are continuous in a row constitute a pair of third routes R3 extending in the extending direction of the arm 21. Therefore, when viewed from the extending direction of the below-described pin 31f, one of the pair of third routes R3 is located at an opposite side of the other of the pair of third routes R3 across the axis of the frame member 31.

A pair of first projecting portions 31d are formed to project from one of the end surfaces of the frame member 31 outward in an extending direction of the frame member 31, and a pair of second projecting portions 31e are formed to project from the other end surface of the frame member 31 outward in the extending direction of the frame member 31. The pair of first projecting portions 31d of the frame member 31 and the pair of second projecting portions 31e of the adjacent frame member 31 are coupled to each other by a pair of pins 31f lined up on the same straight line. With this, each frame member 31 is coupled to the adjacent frame member 31 so as to be swingable about an axis (swing axis) of the pair of pins 31f. The swing axes of the frame members 31 are parallel to one another, and the first bending joint 27 performs such a bending operation that a distal end 27b of the first bending joint 27 turns toward a direction (hereinafter also referred to as the bending direction) perpendicular to the axis of the frame member 31 and the swing axis. In FIG. 6A, the axis of the frame member 31 denotes an axis extending in a paper surface leftward/rightward direction, and the swing axis denotes an axis extending in a paper surface depth direction.

As described above, when viewed from the extending direction of the below-described pin 31f, one of the pair of second routes R2 is located at an opposite side of the other of the pair of second routes R2 across the axis of the frame member 31. Therefore, when the first bending joint 27 performs the bending operation, the route length of the second route R2 located at a bending-direction inner side out of the pair of second routes R2 becomes short, and the route length of the second route R2 located at a bending-direction outer side becomes long. Similarly, when viewed from the extending direction of the below-described pin 31f, one of the pair of third routes R3 is located at an opposite side of the other of the pair of third routes R3 across the axis of the frame member 31. Therefore, when the first bending joint 27 performs the bending operation, the route length of the third route R3 located at the bending-direction inner side out of the pair of third routes R3 becomes short, and the route length of the third route R3 located at the bending-direction outer side becomes long.

Since the second bending joint 28 is the same in configuration as the first bending joint 27, an explanation thereof is omitted.

The connecting portion 29 is a hollow tubular body and connects the first bending joint 27 and the second bending joint 28.

The wrist joint 30 rotates the end effector 22 around an axis L2 of the distal end 21b of the arm 21. The wrist joint 30 is a plate-shaped body extending on a plane perpendicular to an axis of the arm 21 (axis of the joint portion 26) and is provided with a through hole 30a at a center portion of the wrist joint 30, the through hole 30a connecting a proximal end surface of the wrist joint 30 and a distal end surface of the wrist joint 30. The through hole 30a is a hole through which a below-described end effector operating cable 43 is inserted. The through hole 30a is formed on an axis of the distal end 21b of the arm 21. The wrist joint 30 is attached to a distal end 28b of the second bending joint 28 through a bearing (not shown) so as to be continuous with the distal end 28b. Therefore, the wrist joint 30 is configured to be rotatable around the axis L2 of the distal end 21b of the arm 21 relative to the flexible shaft 25, the first bending joint 27, and the second bending joint 28.

A distal end 44b of the below-described torque transmission tube 44 is fixed to the proximal end surface of the wrist joint 30, i.e., a peripheral portion of the through hole 30a (see FIG. 7).

The end effector 22 is a surgical tool. In the present embodiment, the end effector 22 is the forceps. The end effector 22 is attached to the distal end surface of the wrist joint 30. To be specific, the end effector 22 is continuous with a distal end of the joint portion 26 (i.e., the distal end 28b of the second bending joint 28).

The end effector 22 includes an opening/closing operating mechanism (not shown) including an operating cable coupling portion. The operating cable coupling portion is a portion to which a distal end 43b of the below-described end effector operating cable 43 is coupled. The opening/closing operating mechanism of the end effector 22 is a Mechanism configured to, when the operating cable coupling portion is moved in a predetermined direction, open or close the forceps by a predetermined amount in accordance with a movement distance of the operating cable coupling portion. The operating cable coupling portion is biased by a biasing mechanism (not shown) in a direction from a proximal end 43a of the end effector operating cable 43 toward the distal end 43b. With this, when the end effector operating cable 43 is pulled in a direction from the distal end 43b to the proximal end 43a, the operating cable coupling portion is moved in a movement direction of the distal end 43b of the end effector operating cable 43 against the biasing force of the biasing mechanism. Thus, the end effector 22 performs, for example, a closing operation to perform a holding operation of a target. Further, when the end effector operating cable 43 is sent out in a direction from the proximal end 43a to the distal end 43b, the end effector operating cable 43 is slackened. However, the biasing mechanism moves the operating cable coupling portion in a direction opposite to the movement direction of the distal end 43b of the end effector operating cable 43 so as to absorb the slackening of the end effector operating cable 43. Thus, the end effector 22 performs, for example, an opening operation to perform a releasing operation of the target.

As above, an internal space from the proximal end 21a to the distal end 21b of the arm 21 is a communicating space, and the first bending joint operating cable 41, the second bending joint operating cable 42, the end effector operating cable 43, and the torque transmission tube 44 in the below-described driving force transmission mechanism 24 are inserted through this internal space.

The driving force transmission mechanism 24 is a mechanism configured to transmit driving force of the below-described robot main body driving mechanism 51 of the driving portion 3 to mechanisms continuous with the distal end 25b of the flexible shaft 25, i.e., to the first bending joint 27, the second bending joint 28, the wrist joint 30, and the end effector 22. As shown in FIG. 4, the driving force transmission mechanism 24 includes a first bending joint driving force transmission portion 45, a second bending joint driving force transmission portion 46, an end effector driving force transmission portion 47, and a wrist joint driving force transmission portion 48.

The first bending joint driving force transmission portion 45 is a mechanism configured to transmit driving force of a below-described first bending joint driving portion 35 (see FIG. 3) of the driving portion 3 to the first bending joint 27. The first bending joint driving force transmission portion 45 includes the first bending joint operating cable 41, a first rotating shaft 63, a first bending joint operating cable pulling pulley 61, and the driven-side first bending joint driving rotating body 62. The first rotating shaft 63, the first bending joint operating cable pulling pulley 61, and the driven-side first bending joint driving rotating body 62 are provided in the base 23.

Figure 8A:
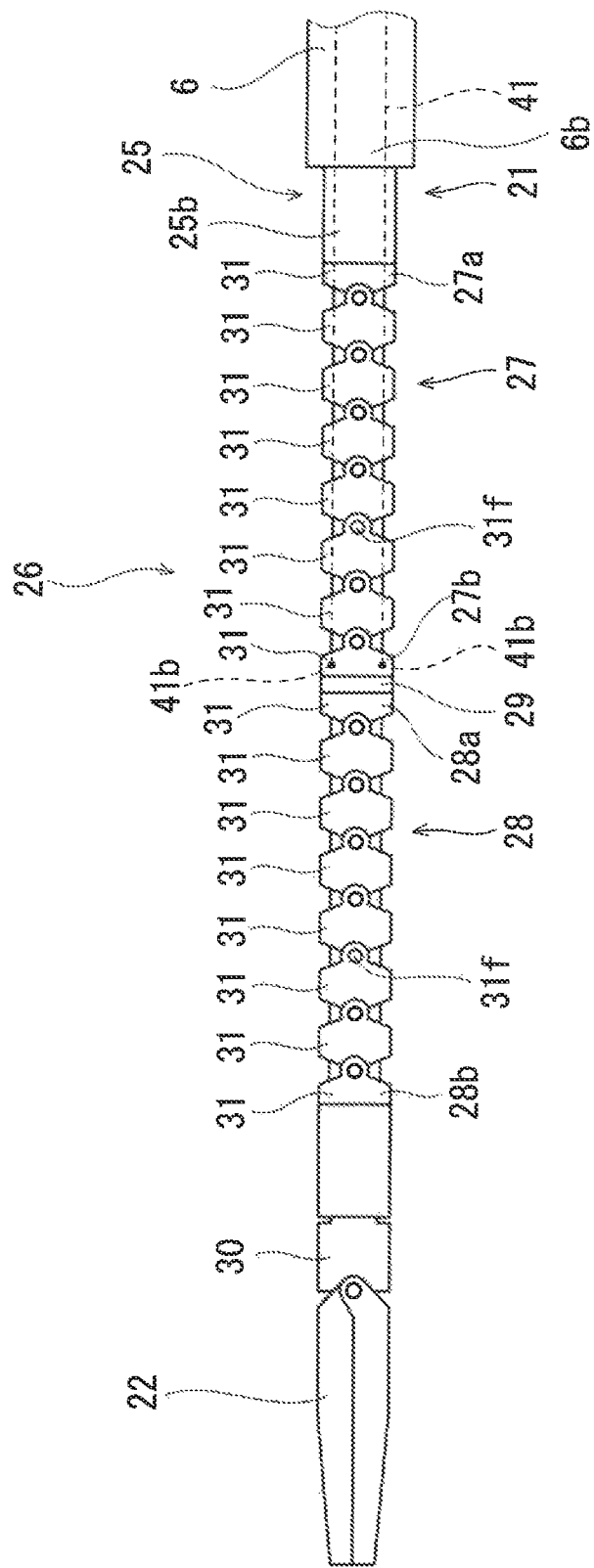
FIG. 8A is a diagram showing a configuration example of the distal end of the robot main body of the surgical robot of FIG. 1 and is a diagram showing a configuration example of a first bending joint operating cable.

FIG. 8A is a diagram showing a configuration example of the distal end of the robot main body 2 and is a diagram showing a configuration example of the first bending joint operating cable 41.

As shown in FIG. 8A, both end portions 41b of the first bending joint operating cable 41 are fixed to the frame member 31 located at the distal end 27b of the first bending joint 27.

A part of the first bending joint operating cable 41 which part extends from one of the end portions 41b to an intermediate portion 41a of the first bending joint operating cable 41 extends through an internal space of one of the pair of second routes R2 of the first bending joint 27 and the internal space of the flexible shaft 25 to reach the internal space of the base 23. As shown in FIGS. 4 and 5, in the internal space of the base 23, the first bending joint operating cable 41 is wound around one of the pair of first bending joint operating cable direction changing pulleys 78. A part of the first bending joint operating cable 41 which part extends from this wound portion to the intermediate portion 41a extends on a virtual plane perpendicular to the axis L1.

Further, a part of the first bending joint operating cable 41 which part extends from the other end portion 41b to the intermediate portion 41a extends through an internal space of the other of the pair of second routes R2 of the first bending joint 27 and the internal space of the flexible shaft 25 to reach the internal space of the base 23. In the internal space of the base 23, the first bending joint operating cable 41 is wound around the other of the pair of first bending joint operating cable direction changing pulleys 78. A part of the first bending joint operating cable 41 which part extends from this wound portion to the intermediate portion 41a extends on the same virtual plane as the plane perpendicular to the axis L1.

The first rotating shaft 63 is a shaft extending in a direction along the axis L3 parallel to the axis L1. Both end portions of the first rotating shaft 63 is attached to the base 23 through bearings, and the first rotating shaft 63 is supported so as to be rotatable relative to the base 23 around the axis L3.

The first bending joint operating cable pulling pulley 61 rotates to move the first bending joint operating cable 41 in the extending direction of the first bending joint operating cable 41. In the present embodiment, the first bending joint operating cable pulling pulley 61 is provided on a virtual plane on which a part of the first bending joint operating cable 41 which part extends from each of the wound portions, wound around the respective first bending joint operating cable direction changing pulleys 78, to the intermediate portion 41a extends. The first bending joint operating cable pulling pulley 61 is fixed to an end portion of the first rotating shaft 63, the end portion being located close to the arm-side end plate 77 of the base 23. The first bending joint operating cable pulling pulley 61 is configured to be rotatable around the axis L3 integrally with the first rotating shaft 63. The intermediate portion 41a of the first bending joint operating cable 41 is wound around and fixed to the first bending joint operating cable pulling pulley 61. With this, the first bending joint operating cable 41 can be smoothly driven by the first bending joint operating cable pulling pulley 61.

The driven-side first bending joint driving rotating body 62 is fixed to an end portion of the first rotating shaft 63, the end portion being located close to the driving portion-side end plate 76. The driven-side first bending joint driving rotating body 62 is located at the first through hole 76a of the driving portion-side end plate 76. The driven-side first bending joint driving rotating body 62 is formed in a circular plate shape. Driven-side engagement portions 62a are provided on a surface of the driven-side first bending joint driving rotating body 62, the surface facing the robot main body driving mechanism 51 with the base 23 attached to the robot main body driving mechanism 51. The driven-side engagement portions 62a are portions engaged with driving-side engagement portions 91a (see FIG. 3) of a below-described driving-side first bending joint rotating body 91a. In the present embodiment, the driven-side engagement portions 62a are two projections projecting in a direction along the axis L1. When the driven-side first bending joint driving rotating body 62 is rotated in a predetermined rotational direction by the driving force of the below-described first bending joint driving portion 35, the driven-side first bending joint driving rotating body 62 and the first bending joint operating cable pulling pulley 61 are integrally rotated in the predetermined rotational direction. Then, a part of the first bending joint operating cable 41 which part extends from the intermediate portion 41a to one of the end portions 41b is pulled, and the one end portion 41b moves toward the proximal end 21a of the arm 21. With this, the route length of one of the pair of second routes R2 of the first bending joint 27 becomes short, the one second route R2 being a route through which the part of the first bending joint operating cable 41 which part extends from the intermediate portion 41a to the one end portion 41b is inserted. Thus, the first bending joint 27 performs the bending operation of bending toward a side where the one second route R2 is located. Further, by the rotation of the first bending joint operating cable pulling pulley 61, a part of the first bending joint operating cable 41 which part extends from the intermediate portion 41a to the other end portion 41b is sent out to be sent into the other second route R2 which is increased in the route length out of the pair of second routes R2. Further, when the driven-side first bending joint driving rotating body 62 is rotated by the driving force of the below-described first bending joint driving portion 35 in a direction opposite to the predetermined rotational direction, the first bending joint operating cable pulling pulley 61 is rotated in the direction opposite to the predetermined rotational direction. Then, the part of the first bending joint operating cable 41 which part extends from the intermediate portion 41a to the other end portion 41b is pulled, and the other end portion 41b moves toward the proximal end 21a of the arm 21. With this, the route length of the other of the pair of second routes R2 of the first bending joint 27 becomes short, the other second route R2 being a route through which the part of the first bending joint operating cable 41 which part extends from the intermediate portion 41a to the other end portion 41b is inserted. Thus, the first bending joint 27 performs the bending operation of bending toward a side where the other second route R2 is located. Further, by the rotation of the first bending joint operating cable pulling pulley 61, the part of the first bending joint operating cable 41 which part extends from the intermediate portion 41a to the one end portion 41b is sent out to be sent into the one second route R2 which is increased in the route length out of the pair of second routes R2.

The second bending joint driving force transmission portion 46 is a mechanism configured to transmit driving force of a below-described second bending joint driving portion 36 (see FIG. 3) of the driving portion 3 to the second bending joint 28. The second bending joint driving force transmission portion 46 includes the second bending joint operating cable 42, a second rotating shaft 66, a second bending joint operating cable pulling pulley 64, and the driven-side second bending joint driving rotating body 65. The second rotating shaft 66, the second bending joint operating cable pulling pulley 64, and the driven-side second bending joint driving rotating body 65 are provided in the base 23.

Figure 8B:
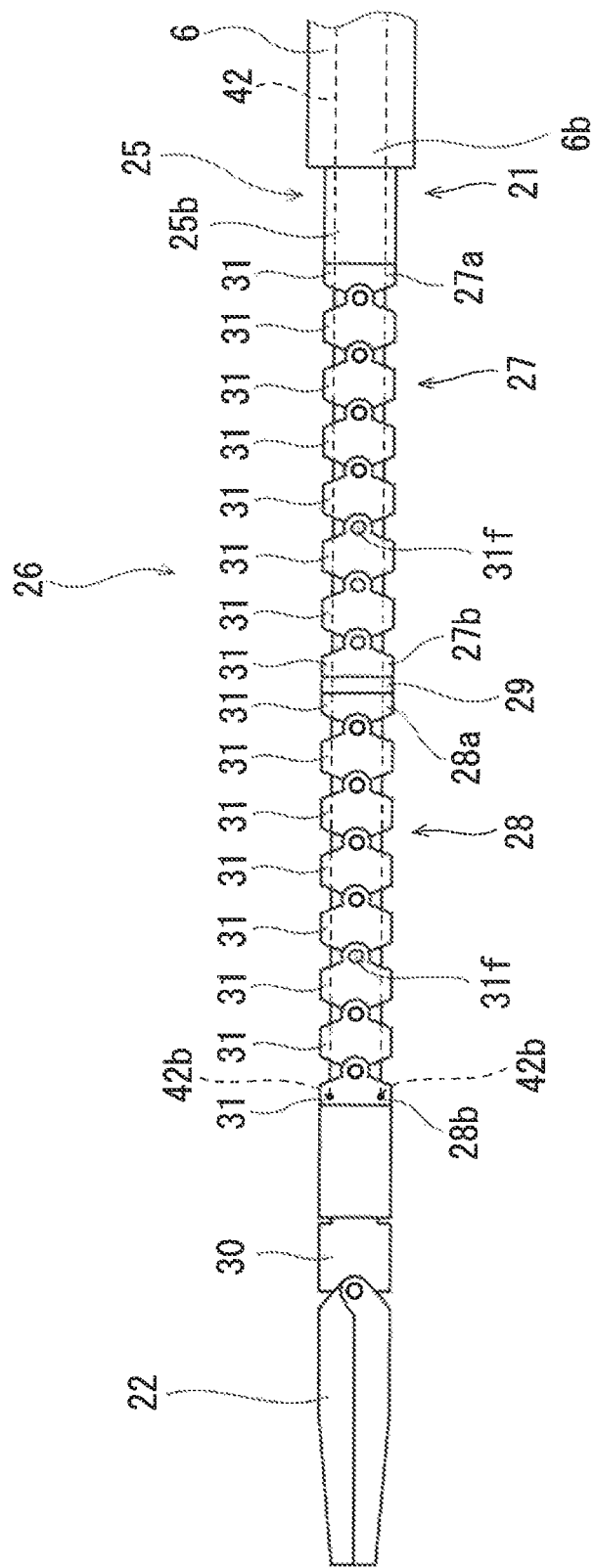
FIG. 8B is a diagram showing a configuration example of the distal end of the robot main body of the surgical robot of FIG. 1 and is a diagram showing a configuration example of a second bending joint operating cable.

FIG. 8B is a diagram showing a configuration example of the distal end of the robot main body 2 and is a diagram showing a configuration example of the second bending joint operating cable 42.

As shown in FIG. 8B, both end portions 42b of the second bending joint operating cable 42 are fixed to the frame member 31 located at the distal end 28b of the second bending joint 28. A part of the second bending joint operating cable 42 which part extends from one of the end portions 42b to an intermediate portion 42a of the second bending joint operating cable 42 extends through an internal space of one of the pair of third routes R3 of the second bending joint 28, an internal space of the connecting portion 29, an internal space of one of the pair of third routes R3 of the first bending joint 27, and the internal space of the flexible shaft 25 to reach the internal space of the base 23. As shown in FIGS. 4 and 5, in the internal space of the base 23, the second bending joint operating cable 42 is wound around one of the pair of second bending joint operating cable direction changing pulleys 79. A part of the second bending joint operating cable 42 which part extends from this wound portion to the intermediate portion 42a extends on the virtual plane perpendicular to the axis L1.

Further, a part of the second bending joint operating cable 42 which part extends from the other end portion 42b to the intermediate portion 42a extends through an internal space of the other of the pair of third routes R3 of the second bending joint 28, the internal space of the connecting portion 29, an internal space of the other of the pair of third routes R3 of the first bending joint 27, and the internal space of the flexible shaft 25 to reach the internal space of the base 23. In the internal space of the base 23, the second bending joint operating cable 42 is wound around the other of the pair of second bending joint operating cable direction changing pulleys 79. A part of the second bending joint operating cable 42 which part extends from this wound portion to the intermediate portion 42a extends on the same virtual plane as the plane perpendicular the axis L1.

The second rotating shaft 66 is a shaft extending in a direction along the axis L4 parallel to the axis L1. Both end portions of the second rotating shaft 66 are attached to the base 23 through bearings, and the second rotating shaft 66 is supported so as to be rotatable relative to the base 23 around the axis L4. The axis L4 is located at a position where the axis L3 reaches by being rotated about the axis L1 by about 180 degrees.

The second bending joint operating cable pulling pulley 64 rotates to move the second bending joint operating cable 42 in the extending direction of the second bending joint operating cable 42. In the present embodiment, the second bending joint operating cable pulling pulley 64 is provided on a virtual plane on which a part of the second bending joint operating cable 42 which part extends from each of the wound portions, wound around the respective second bending joint operating cable direction changing pulleys 79, to the intermediate portion 42a extends. The second bending joint operating cable pulling pulley 64 is fixed to an end portion of the second rotating shaft 66, the end portion being located close to the arm-side end plate 77 of the base 23. The second bending joint operating cable pulling pulley 64 is configured to be rotatable around the axis L4 integrally with the second rotating shaft 66. The intermediate portion 42a of the second bending joint operating cable 42 is wound around and fixed to the second bending joint operating cable pulling pulley 64. With this, the second bending joint operating cable 42 can be smoothly driven by the second bending joint operating cable pulling pulley 64.

As described above, the pair of first bending joint operating cable direction changing pulleys 78 and the pair of second bending joint operating cable direction changing pulleys 79 are provided so as to be different in position in the direction along the axis L1 from each other. Further, the virtual plane on which the part of the first bending joint operating cable 41 which part extends from each of the wound portions, wound around the respective first bending joint operating cable direction changing pulleys 78, to the intermediate portion 41a extends is different from the virtual plane on which the part of the second bending joint operating cable 42 which part extends from each of the wound portions, wound around the respective second bending joint operating cable direction changing pulleys 79, to the intermediate portion 42a extends. Therefore, the first bending joint operating cable 41 and the second bending joint operating cable 42 are prevented from contacting each other.

The driven-side second bending joint driving rotating body 65 is fixed to an end portion of the second rotating shaft 66, the end portion being located close to the driving portion-side end plate 76. The driven-side second bending joint driving rotating body 65 is located at the second through hole 76b of the driving portion-side end plate 76. The driven-side second bending joint driving rotating body 65 is formed in a circular plate shape. A plurality of driven-side engagement portions 65a are provided on a surface of the driven-side second bending joint driving rotating body 65, the surface facing the robot main body driving mechanism 51 with the base 23 attached to the robot main body driving mechanism 51. The driven-side engagement portions 65a are portions engaged with driving-side engagement portions 92a (see FIG. 3) of a below-described driving-side second bending joint rotating body 92.

In the present embodiment, the driven-side engagement portions 65a are two projections projecting in the direction along the axis L1. When the driven-side second bending joint driving rotating body 65 is rotated in a predetermined rotational direction by the driving force of the below-described second bending joint driving portion 36, the driven-side second bending joint driving rotating body 65 and the second bending joint operating cable pulling pulley 64 are integrally rotated in the predetermined rotational direction. Then, a part of the second bending joint operating cable 42 which part extends from the intermediate portion 42a to one of the end portions 42b is pulled, and the one end portion 42b moves toward the proximal end 21a of the arm 21. With this, the route length of one of the pair of third routes R3 of the second bending joint 28 becomes short, the one third route R3 being a route through which the part of the second bending joint operating cable 42 which part extends from the intermediate portion 42a to the one end portion 42b is inserted. Thus, the second bending joint 28 performs the bending operation of bending toward a side where the one third route R3 is located. Further by the rotation of the second bending joint operating cable pulling pulley 64, a part of the second bending joint operating cable 42 which part extends from the intermediate portion 42a to the other end portion 42b is sent out to be sent into the other third route R3 which is increased in the route length out of the pair of third routes R3.

Further, when the driven-side second bending joint driving rotating body 65 is rotated by the driving force of the below-described second bending joint driving portion 36 in a direction opposite to the predetermined rotational direction, the second bending joint operating cable pulling pulley 64 is rotated in the direction opposite to the predetermined rotational direction. Then, the part of the second bending joint operating cable 42 which part extends from the intermediate portion 42a to the other end portion 42b is pulled, and the other end portion 42b moves toward the proximal end 21a of the arm 21. With this, the route length of the other of the pair of third routes R3 of the second bending joint 28 becomes short, the other third route R3 being a route through which the part of the second bending joint operating cable 42 which part extends from the intermediate portion 42a to the other end portion 42b is inserted. Thus, the second bending joint 28 performs the bending operation of bending toward a side where the other third route R3 is located. Further, by the rotation of the second bending joint operating cable pulling pulley 64, the part of the second bending joint operating cable 42 which part extends from the intermediate portion 42a to the one end portion 42b is sent out to be sent into the one third route R3 which is increased in the route length out of the pair of third routes R3.

The end effector driving force transmission portion 47 is a mechanism configured to transmit driving force of a below-described end effector driving portion 37 (see FIG. 3) of the driving portion 3 to the end effector 22. The end effector driving force transmission portion 47 includes the end effector operating cable 43, a third rotating shaft 69, an end effector operating cable pulling pulley 67, and the driven-side end effector driving rotating body 68. The third rotating shaft 69, the end effector operating cable pulling pulley 67, and the driven-side end effector driving rotating body 68 are provided in the base 23.

As described above, the distal end 43b of the end effector operating cable 43 is coupled to the end effector 22. A part of the end effector operating cable 43 which part extends from the distal end 43b to the proximal end 43a extends through the through hole 30a (see FIG. 7) of the wrist joint 30 and an internal space of the torque transmission tube 44 (i.e., the internal spaces of the joint portion 26 and the flexible shaft 25), and the proximal end 43a is located in the internal space of the base 23. To be specific, the end effector operating cable 43 is inserted through the torque transmission tube 44.

The third rotating shaft 69 is a shaft extending in the direction along the axis L1. One end portion of the third rotating shaft 69 is attached to the projecting portion 76c of the base 23 through a bearing and is supported so as to be rotatable relative to the base 23 around the axis L1, the end portion being located close to the robot main body driving mechanism 51 with the base 23 attached to the robot main body driving mechanism 51. A part of the third rotating shaft 69 which part extends from the other end portion toward the one end portion is attached to and supported by the coupling portion 70 of the below-described wrist joint driving force transmission portion 48 through a bearing and is configured to be rotatable around the axis L1. Since the coupling portion 70 is configured to be rotatable relative to the base 23 around the axis L1 as described below, the other end portion of the third rotating shaft 69 is indirectly attached to the base 23 through the coupling portion 70 and is supported so as to be rotatable relative to the base 23 around the axis L1. The other end portion of the third rotating shaft 69 is located in the coupling portion 70.

The end effector operating cable pulling pulley 67 rotates to move the end effector operating cable 43 in an extending direction of the end effector operating cable 43. In the present embodiment, the end effector operating cable pulling pulley 67 is fixed to the other end portion of the third rotating shaft 69 and is configured to be rotatable relative to the base 23 around the axis L1. Therefore, the end effector operating cable pulling pulley 67 is provided in an internal space of the coupling portion 70. The proximal end 43a of the end effector operating cable 43 is held by and wound around the end effector operating cable pulling pulley 67. Therefore, the end effector operating cable pulling pulley 67 rotates to wind and unwind the proximal end 43a of the end effector operating cable 43.

The driven-side end effector driving rotating body 68 is, for example, a spur gear. The driven-side end elector driving rotating body 68 is fixed to the one end portion of the third rotating shaft 69 and is located in the projecting portion 76c. The teeth of the driven-side end effector driving rotating body 68 are exposed from a portion where the peripheral wall 76d of the projecting portion 76c is removed. With the base 23 attached to the robot main body driving mechanism 51, the driven-side end effector driving rotating body 68 meshes with and is connected to teeth of a below-described driving-side end effector driving rotating body 94 (see FIG. 3). When the driven-side end effector driving rotating body 68 is rotated in a predetermined rotational direction by the driving force of the below-described end effector driving portion 37, the driven-side end effector driving rotating body 68 and the end effector operating cable pulling pulley 67 are integrally rotated in the predetermined rotational direction, and the end effector operating cable 43 is pulled. Thus, the end effector 22 performs the holding operation. Further, when the driven-side end effector driving rotating body 68 is rotated by the driving force of the below-described end effector driving portion 37 in a direction opposite to the predetermined rotational direction, the end effector operating cable pulling pulley 67 is rotated in the direction opposite to the predetermined rotational direction, and the proximal end 43a of the end effector operating cable 43 is sent out. Thus, the end effector 22 performs the releasing operation.

The wrist joint driving force transmission portion 48 is a mechanism configured to transmit driving force of a below-described wrist joint driving portion 38 (see FIG. 3) of the driving portion 3 to the wrist joint 30. The wrist joint driving force transmission portion 48 includes the torque transmission tube 44, the coupling portion 70, and the driven-side wrist joint driving rotating body 71. The coupling portion 70 and the driven-side wrist joint driving rotating body 71 are provided in the base 23.

FIG. 7 is a partial breakaway view showing a configuration example of the wrist joint 30.

The torque transmission tube 44 has flexibility and is formed in a tubular shape. The torque transmission tube 44 can transmit torque, applied to the proximal end 44a thereof, to the distal end 44b directed in an arbitrary direction. To be specific, the torque transmission tube 44 is configured such that by rotating the proximal end 44a, the distal end 44b is rotated in accordance with a rotation amount of the proximal end 44a through an intermediate portion thereof bent in an arbitrary shape. As shown in FIG. 7, the distal end 44b of the torque transmission tube 44 is fixed to a peripheral portion of the through hole 30a of the wrist joint 30. A part of the torque transmission tube 44 which part extends from the distal end 44b to the proximal end 44a extends through an internal space of the first route R1 of the second bending joint 28, the internal space of the connecting portion 29, an internal space of the first route R1 of the first bending joint 27, and the internal space of the flexible shaft 25, and the proximal end 44a of the torque transmission tube 44 is located in the internal space of the base 23.

The end effector operating cable 43 extends from the end effector 22 through the through hole 30a of the wrist joint 30 to be inserted into the internal space of the torque transmission tube 44 through the distal end 44b of the torque transmission tube 44. The end effector operating cable 43 further extends through the internal space of the torque transmission tube 44 to the base 23. In the internal space of the base 23, the end effector operating cable 43 is led out from the proximal end 44a of the torque transmission tube 44 to an outside of the torque transmission tube 44. Therefore, the end effector operating cable 43 extends along a central axis of the torque transmission tube 44 or its vicinity. The route length from the proximal end 44a of the torque transmission tube 44 to the distal end 44b along the central axis hardly changes between when the arm 21 is stretched and when the arm 21 is bent. Therefore, it is possible to prevent a case where by bending the arm 21, the end effector operating cable 43 is moved in the extending direction, and this operates the end effector 22. Further, it is possible to prevent a case where the end effector operating cable 43 contacts the first bending joint operating cable 41 and the second bending joint operating cable 42 and also possible to prevent a case where when the first bending joint operating cable 41 or the second bending joint operating cable 42 operates, the end effector operating cable 43 unexpectedly operates.

The first bending joint operating cable 41 and the second bending joint operating cable 42 extend through a space between the flexible shaft 25 and the torque transmission tube 44 to reach the base 23. Therefore, the operations of the first bending joint operating cable 41 and the second bending joint operating cable 42 and the operations of the end effector operating cable 43 and the torque transmission tube 44 can be separated from each other. On this account, the first bending joint 27 and the second bending joint 28 can be operated independently from the operations of the end effector 22 and the wrist joint 30.

Since a part of the torque transmission tube 44 which part extends between the proximal end 44a and the distal end 44b has flexibility, the part is bendable together with the flexible shaft 25.

The coupling portion 70 is a tubular body having an axis extending in the direction along the axis L1. One end portion of the coupling portion 70 is attached to and supported by the third rotating shaft 69 of the end effector driving force transmission portion 47 through a bearing, the end portion being located close to the robot main body driving mechanism 51 with the base 23 attached to the robot main body driving mechanism 51. Since the third rotating shaft 69 is configured to be rotatable relative to the base 23 around the axis L1 as described above, the one end portion of the coupling portion 70 is indirectly attached to the base 23 through the third rotating shaft 69 and is supported so as to be rotatable relative to the base 23 around the axis L1. The other end portion of the coupling portion 70 is attached to the supporting portion 75a of the base 23 through a bearing and is supported so as to be rotatable relative to the base 23 around the axis L1. Therefore, the coupling portion 70 is configured to be rotatable relative to the base 23 around the axis L1 independently from the operation of the end effector driving force transmission portion 47.

The proximal end 44a of the torque transmission tube 44 is fixed to a peripheral edge of the other end portion of the coupling portion 70, and the internal space of the torque transmission tube 44 and the internal space of the coupling portion 70 communicate with each other. The end effector operating cable 43 led out from the proximal end 44a of the torque transmission tube 44 is wound around the end effector operating cable pulling pulley 67 of the end effector driving force transmission portion 47 in the internal space of the coupling portion 70. The coupling portion 70 includes an end effector operating cable direction changing pulley 72 attached to an inner peripheral surface of the coupling portion 70. The end effector operating cable direction changing pulley 72 is a pulley configured to convert the extending direction of a part of the end effector operating cable 43 to a radial direction about the axis L1, the part being led out from the proximal end 44a of the torque transmission tube 44 in the direction along the axis L1. With this, the end effector operating cable pulling pulley 67 can smoothly wind and unwind the end effector operating cable 43.

The driven-side wrist joint driving rotating body 71 is, for example, a spur gear. The driven-side wrist joint driving rotating body 71 is located between the coupling portion 70 and the driven-side end effector driving rotating body 68 in the direction along the axis L1. The driven-side wrist joint driving rotating body 71 is fixed to the coupling portion 70 and located in the projecting portion 76c. Therefore, the driven-side wrist joint driving rotating body 71 is configured to be rotatable around the axis L1 together with the coupling portion 70. To be specific, the driven-side wrist joint driving rotating body 71 is configured to be rotatable around the axis that is the same as the axis around which the driven-side end effector driving rotating body 68 rotates. Therefore, the base 23 can be reduced in size. The teeth of the driven-side wrist joint driving rotating body 71 are exposed from the peripheral wall 76d. With the base 23 attached to the robot main body driving mechanism 51, the driven-side wrist joint driving rotating body 71 meshes with and is connected to teeth of a below-described driving-side wrist joint driving rotating body 93 (see FIG. 3). When the driven-side wrist joint driving rotating body 71 is rotated in a predetermined rotational direction by the driving force of the below-described wrist joint driving portion 38, the proximal end 44a of the torque transmission tube 44 is rotated in the predetermined rotational direction. With this, the distal end 44b of the torque transmission tube 44 is also rotated in the predetermined rotational direction in accordance with the rotation of the proximal end 44a, and the wrist joint 30 is rotated in the predetermined rotational direction. When the driven-side wrist joint driving rotating body 71 is rotated by the driving force of the below-described wrist joint driving portion 38 in a direction opposite to the predetermined rotational direction, the proximal end 44a of the torque transmission tube 44 is rotated in the direction opposite to the predetermined rotational direction. With this, the distal end 44b of the torque transmission tube 44 is rotated in the direction opposite to the predetermined rotational direction in accordance with the rotation of the proximal end 44a, and the wrist joint 30 is rotated in the direction opposite to the predetermined rotational direction.

The driven-side wrist joint driving rotating body 71 includes a through hole 71a formed to penetrate the coupling portion 70 in the direction along the axis L1. The third rotating shaft 69 is inserted through the through hole 71a.

As shown in FIG. 2, the guide pipe 6 is a flexible tubular body and has an inner diameter that is substantially equal to each of a diameter of the flexible shaft 25 and a diameter of the joint portion 26. A length of the guide pipe 6 is shorter than a length of the flexible shaft 25. Therefore, by sending the distal end of the robot main body 2 through the proximal end of the guide pipe 6, the distal end of the robot main body 2 can be sent to the distal end of the guide pipe 6. The guide pipe 6 is configured such that: the inserted surgical robot 1 and the inserted endoscope 101 can be smoothly moved in an extending direction of the guide pipe 6; and the inserted surgical robot 1 and the inserted endoscope 101 can be smoothly rotated around an axis of the guide pipe 6.

In the present embodiment, the guide pipe 6 is formed separately from the collectively bundling pipe 102. However, the guide pipe 6 may be formed integrally with the collectively bundling pipe 102.

Configuration Example of Driving Portion

As shown in FIG. 2, the driving portion 3 includes the robot main body driving mechanism 51 configured to drive the robot main body 2.

As shown in FIG. 3, the robot main body driving mechanism 51 includes the first bending joint driving portion 35, the second bending joint driving portion 36, the wrist joint driving portion 38, the end effector driving portion 37, and a casing 39 accommodating these portions 35 to 38. Each of the first bending joint driving portion 35, the second bending joint driving portion 36, the wrist joint driving portion 38, and the end effector driving portion 37 includes, for example, a servo motor.

By attaching the base 23 to the robot main body driving mechanism 51, the first bending joint driving portion 35 is connected to the first bending joint operating cable pulling pulley 61 (see FIG. 4) to rotate the first bending joint operating cable pulling pulley 61. Further, by detaching the base 23 from the robot main body driving mechanism 51, the first bending joint driving portion 35 is separated from the first bending joint operating cable pulling pulley 61.

In the present embodiment, with the base 23 of the robot main body 2 attached to the robot main body driving mechanism 51, a driving shaft of the first bending joint driving portion 35 extends toward the base 23 of the robot main body 2 and is attached to the casing 39 so as to extend on the axis L3. The driving-side first bending joint rotating body 91 is fixed to a tip end of the driving shaft of the first bending joint driving portion 35. Therefore, the driving-side first bending joint rotating body 91 is rotated by the rotation of the driving shaft of the first bending joint driving portion 35. The driving-side first bending joint rotating body 91 is formed in a circular plate shape. The driving-side engagement portions 91a are provided on a surface of the driving-side first bending joint rotating body 91, the surface facing the base 23 of the robot main body 2 with the base 23 of the robot main body 2 attached to the robot main body driving mechanism 51. The driving-side engagement portions 91a are portions engaged with the driven-side engagement portions 62a of the driven-side first bending joint driving rotating body 62. In the present embodiment, the driving-side engagement portions 91a are two depressions.

By attaching the base 23 to the robot main body driving mechanism 51, the second bending joint driving portion 36 is connected to the second bending joint operating cable pulling pulley 64 (see FIG. 4) to rotate the second bending joint operating cable pulling pulley 64. Further, by detaching the base 23 from the robot main body driving mechanism 51, the second bending joint driving portion 36 is separated from the second bending joint operating cable pulling pulley 64.

In the present embodiment, with the base 23 of the robot main body 2 attached to the robot main body driving mechanism 51, a driving shaft of the second bending joint driving portion 36 extends toward the base 23 of the robot main body 2 and is attached to the casing 39 so as to extend on the axis L4 parallel to the axis L1 of the proximal end 44a of the torque transmission tube 44. The driving-side second bending joint rotating body 92 is fixed to a tip end of the driving shaft of the second bending joint driving portion 36. Therefore, the driving-side second bending joint rotating body 92 is rotated by the rotation of the driving shaft of the second bending joint driving portion 36. The driving-side second bending joint rotating body 92 is formed in a circular plate shape. The driving-side engagement portions 92a are provided on a surface of the driving-side second bending joint rotating body 92, the surface facing the base 23 of the robot main body 2 with the base 23 of the robot main body 2 attached to the robot main body driving mechanism 51. The driving-side engagement portions 92a are portions engaged with the driven-side engagement portions 65a of the driven-side second bending joint driving rotating body 65. In the present embodiment, the driving-side engagement portions 92a are two depressions.

By attaching the base 23 to the robot main body driving mechanism 51, the wrist joint driving portion 38 is connected to the proximal end 44a (see FIG. 4) of the torque transmission tube 44 to rotate the torque transmission tube 44 around the axis of the torque transmission tube 44. Further, by detaching the base 23 from the robot main body driving mechanism 51, the wrist joint driving portion 38 is separated from the torque transmission tube 44.

In the present embodiment, with the base 23 of the robot main body 2 attached to the robot main body driving mechanism 51, a driving shaft of the wrist joint driving portion 38 extends toward the base 23 of the robot main body 2 and is attached to the casing 39 so as to extend on an axis L5 parallel to the axis L1 of the proximal end 44a of the torque transmission tube 44. The driving-side wrist joint driving rotating body 93 is fixed to a tip end of the driving shaft of the wrist joint driving portion 38. Therefore, the driving-side wrist joint driving rotating body 93 is rotated by the rotation of the driving shaft of the wrist joint driving portion 38. The driving-side wrist joint driving rotating body 93 is, for example, a gear. The teeth (not shown) that mesh with the teeth of the driven-side wrist joint driving rotating body 71 (see FIG. 4) are formed on an outer peripheral edge of the driving-side wrist joint driving rotating body 93.

By attaching the base 23 to the robot main body driving mechanism 51, the end effector driving portion 37 is connected to the end effector operating cable pulling pulley 67 (see FIG. 4) to rotate the end effector operating cable pulling pulley 67. Further, by detaching the base 23 from the robot main body driving mechanism 51, the end effector driving portion 37 is separated from the end effector operating cable pulling pulley 67.

In the present embodiment, with the base 23 of the robot main body 2 attached to the robot main body driving mechanism 51, a driving shaft of the end effector driving portion 37 extends toward the base 23 of the robot main body 2 and is attached to the casing 39 so as to extend on an axis L6 parallel to the axis L1 of the proximal end 44a of the torque transmission tube 44. The driving-side end effector driving rotating body 94 is fixed to a tip end of the driving shaft of the end effector driving portion 37. Therefore, the driving-side end effector driving rotating body 94 is rotated by the rotation of the driving shaft of the end effector driving portion 37. The driving-side end effector driving rotating body 94 is, for example, a gear. The teeth (not shown) that mesh with the teeth of the driven-side end effector driving rotating body 68 (see FIG. 4) are formed on an outer peripheral edge of the driving-side end effector driving rotating body 94.

Therefore, the base 23 can be attached to the robot main body driving mechanism 51 by: causing an axis of the base 23 of the robot main body 2 and an axis of the robot main body driving mechanism 51 to coincide with each other; and moving the base 23 in an axial direction. The base 23 and the driving portion casing 50 are provided with fastening members. A state where the base 23 is attached to the robot main body driving mechanism 51 is maintained by the fastening members.

With the base 23 attached to the robot main body driving mechanism 51, the driven-side engagement portions 62a of the driven-side first bending joint driving rotating body 62 are engaged with the driving-side engagement portions 91*a* of the driving-side first bending joint rotating body 91, and the driving-side first bending joint rotating body 91 is connected to the driven-side first bending joint driving rotating body 62. The rotation of the driven-side first bending joint driving rotating body 62 relative to the driving-side first bending joint rotating body 91 around the axis L3 is restricted. Therefore, when the driving-side first bending joint rotating body 91 is rotated by the driving force of the first bending joint driving portion 35, the driven-side first bending joint driving rotating body 62 is rotated, and thus, the driving force of the first bending joint driving portion 35 is transmitted to the first bending joint 27 through the first bending joint driving force transmission portion 45.

With the base 23 attached to the robot main body driving mechanism 51, the driven-side engagement portions 65*a* of the driven-side second bending joint driving rotating body 65 are engaged with the driving-side engagement portions 92*a* of the driving-side second bending joint rotating body 92, and the driving-side second bending joint rotating body 92 is connected to the driven-side second bending joint driving rotating body 65. The rotation of the driven-side second bending joint driving rotating body 65 relative to the driving-side second bending joint rotating body 92 around the axis L4 is restricted. Therefore, when the driving-side second bending joint rotating body 92 is rotated by the driving force of the second bending joint driving portion 36, the driven-side second bending joint driving rotating body 65 is rotated, and thus, the driving force of the second bending joint driving portion 36 is transmitted to the second bending joint 28 through the second bending joint driving force transmission portion 46.

With the base 23 attached to the robot main body driving mechanism 51, the teeth of the driving-side end effector driving rotating body 94 mesh with the teeth of the driven-side end effector driving rotating body 68, and the driving-side end effector driving rotating body 94 is connected to the driven-side end effector driving rotating body 68. Therefore, when the driving-side end effector driving rotating body 94 is rotated by the driving force of the end effector driving portion 37, the driven-side end effector driving rotating body 68 is rotated, and thus, the driving force of the end effector driving portion 37 is transmitted to the end effector 22 through the end effector driving force transmission portion 47.

With the base 23 attached to the robot main body driving mechanism 51, the teeth of the driving-side wrist joint driving rotating body 93 mesh with the teeth of the driven-side wrist joint driving rotating body 71, and the driving-side wrist joint driving rotating body 93 is connected to the driven-side wrist joint driving rotating body 71. Therefore, when the driving-side wrist joint driving rotating body 93 is rotated by the driving force of the wrist joint driving portion 38, the driven-side wrist joint driving rotating body 71 is rotated, and thus, the driving force of the wrist joint driving portion 38 is transmitted to the wrist joint 30 through the wrist joint driving force transmission portion 48.

When replacing the robot main body 2, the base 23 of the robot main body 2 can be detached from the robot main body driving mechanism 51, and the base 23 of the different robot main body 2 can be attached to the robot main body driving mechanism 51. Thus, the robot main body 2 can be replaced quickly.

Configuration Examples of Control Unit and Operating Portion

Figure 10:
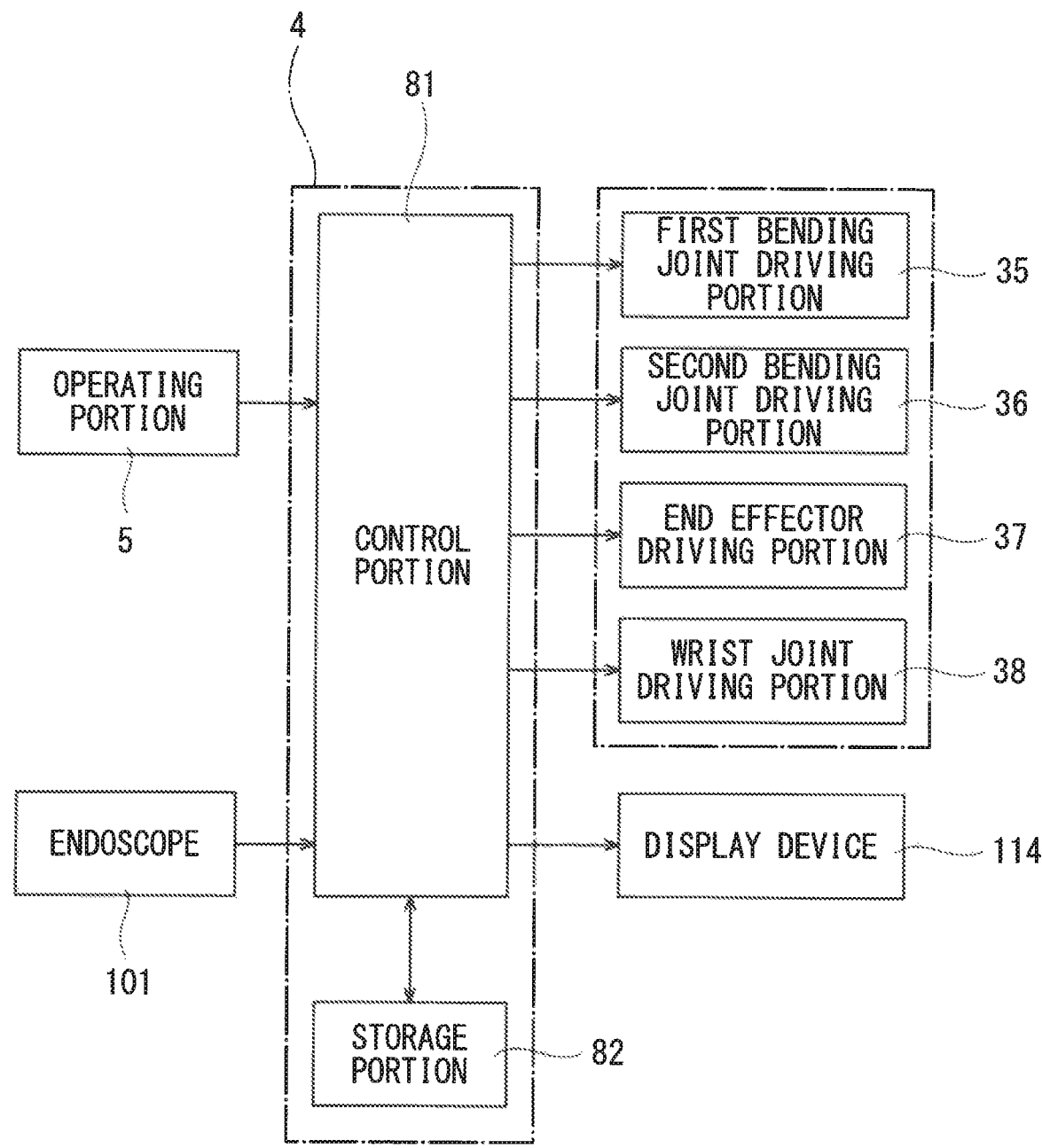
FIG. 10 is a block diagram schematically showing a configuration example of a control system of the surgical robot of FIG. 1.

FIG. 10 is a block diagram showing a configuration example of the control unit 4.

The control unit 4 included in the robot main body 2 includes: a control portion 81 including a calculation unit, such as a CPU; and a storage portion 82 including a memory, such as ROM or RAM. The control portion 81 may be constituted by a single control unit which performs centralized control or may be constituted by a plurality of control units which cooperate to perform distributed control. Based on data received from the operating portion 5, the control portion 81 controls operations of the first bending joint driving portion 35, second bending joint driving portion 36, end effector driving portion 37, and wrist joint driving portion 38 of the robot main body driving mechanism 51 of the surgical robot 1 to control an operation of the surgical robot 1. Further, the control portion 81 processes image data, received from the endoscope 101, to transmit the processed image data to the display device 114. The storage portion 82 stores predetermined control programs, and the control portion 81 reads out and executes the control programs to control the operation of the surgical robot 1.

The operator W operates the operating portion 5 to input an operation instruction to be executed by the surgical robot 1. The operating portion 5 is configured to be communicable with the control portion 81. The operating portion 5 converts the operation instruction to be executed by the surgical robot 1 into data to transmit the data to the control portion 81, the operation instruction being input by the operator W. Based on the received operation instruction to be executed by the surgical robot 1, the control portion 81 generates respective operations to be executed by the first bending joint driving portion 35, the second bending joint driving portion 36, the end effector driving portion 37, and the wrist joint driving portion 38. Then, the control portion 81 controls the operations of the first bending joint driving portion 35, the second bending joint driving portion 36, the end effector driving portion 37, and the wrist joint driving portion 38 in accordance with the above generated operations.

Example of Use

Next, an example of use of the surgical robot 1 will be explained.

First, as shown in FIG. 2, one or more guide pipes 6 are inserted into the collectively bundling pipe 102 through an opening of a proximal end 102*a* of the collectively bundling pipe 102 and are sent into the collectively bundling pipe 102 until the distal end 6*b* of the guide pipe 6 projects from a distal end 102*b* of the collectively bundling pipe 102. Similarly, the endoscope 101 is sent into the collectively bundling pipe 102 until a distal end of the endoscope 101 projects from the distal end 102*b* of the collectively bundling pipe 102.

Next, a trocar 110 is placed on a part of a body surface of the patient P, one or more surgical robots 1 and the endoscope 101 being inserted into the part of the body surface.

Next, the collectively bundling pipe 102 is inserted into the trocar 110 placed on the body surface of the patient P. Then, the inside of the body of the patient P is visually recognized by the endoscope 101, and the distal end 102*b* of the collectively bundling pipe 102 is located in the vicinity of a treated part of the patient P. The collectively bundling pipe 102, the endoscope 101, and the guide pipe 6 have flexibility. Therefore, for example, even when an organ of the patient P is located on a virtual straight line passing through the part on which the trocar 110 is placed and the treated part, the collectively bundling pipe 102, the endoscope 101, and the guide pipe 6 can be curved to bypass the organ. Thus, the distal end 102b of the collectively bundling pipe 102 can be introduced to the vicinity of the treated part.

Next, the arm 21 of the robot main body 2 of each of the one or more surgical robots 1 is inserted into the guide pipe 6 through an opening of the proximal end 6a of the guide pipe 6 and is sent into the guide pipe 6 until the distal end 21b of the arm 21 projects from the distal end 6b of the guide pipe 6. With this, the one or more surgical robots 1 and the endoscope 101 can be collectively bundled by the collectively bundling pipe 102 to be integrally introduced to the vicinity of the treated part of the patient P.

Next, the base 23 is attached to the robot main body driving mechanism 51, and with this, the driving force transmission mechanism 24 of the robot main body 2 and the robot main body driving mechanism 51 are coupled to each other. Thus, the driving force of the robot main body driving mechanism 51 is transmitted to the first bending joint 27, the second bending joint 28, the end effector 22, and the wrist joint 30 through the first bending joint driving force transmission portion 45, second bending joint driving force transmission portion 46, end effector driving force transmission portion 47, and wrist joint driving force transmission portion 48 of the driving force transmission mechanism 24.

Next, the operator W operates the operating portion 5 while confirming the image taken by the video camera of the endoscope 101 and displayed on the display device 114. Then, based on the data received from the operating portion 5, the control portion 81 controls the operations of the first bending joint driving portion 35, second bending joint driving portion 36, end effector driving portion 37, and wrist joint driving portion 38 of the robot main body driving mechanism 51 to control the operation of the surgical robot 1.

At this time, when the control portion 81 determines that the operation instruction to be executed by the surgical robot 1 contains an operation instruction of bending the first bending joint 27, the control portion 81 drives the first bending joint driving portion 35 of the robot main body driving mechanism 51 to bend the first bending joint 27. With this, the end effector 22 moves in the bending direction of the first bending joint 27.

Further, when the control portion 81 determines that the operation instruction to be executed by the surgical robot 1 contains an operation instruction of bending the second bending joint 28, the control portion 81 drives the second bending joint driving portion 36 of the robot main body driving mechanism 51 to bend the second bending joint 28. With this, the end effector 22 moves in the bending direction of the second bending joint 28.

Further, when the control portion 81 determines that the operation instruction to be executed by the surgical robot 1 contains an operation instruction of causing the end effector 22 to perform the holding operation or the releasing operation, the control portion 81 drives the end effector driving portion 37 of the robot main body driving mechanism 51 to cause the end effector 22 to perform the holding operation or the releasing operation.

Further, when the control portion 81 determines that the operation instruction to be executed by the surgical robot 1 contains an operation instruction of rotating the wrist joint 30, the control portion 81 drives the wrist joint driving portion 38 of the robot main body driving mechanism 51 to rotate the wrist joint 30. As above, the wrist joint 30 is rotated by the rotation of the torque transmission tube 44 which can rotate the distal end 44b in accordance with the rotation amount of the proximal end 44a through the intermediate portion thereof bent in an arbitrary shape. Therefore, even when the flexible shaft 25 and the torque transmission tube 44 are in a bent state, or even while bending the flexible shaft 25 and the torque transmission tube 44, the wrist joint 30 can be accurately rotated.

The holding operation and releasing operation of the end effector 22 are performed in such a manner that the control portion 81 controls an angular position of the end effector operating cable pulling pulley 67 around the axis L1 relative to an angular position of the coupling portion 70 around the axis. For example, when rotating only the wrist joint 30 without causing the end effector 22 to perform the holding operation or the releasing operation, the control portion 81 rotates the driven-side end effector driving rotating body 68 and the driven-side wrist joint driving rotating body 71 in synchronization with each other such that an angular position of the driven-side wrist joint driving rotating body 71 relative to the driven-side end effector driving rotating body 68 does not change. With this, an angular position of the end effector operating cable direction changing pulley 72 around the axis L1 relative to the end effector operating cable pulling pulley 67 of the end effector driving force transmission portion 47 does not change, the end effector operating cable direction changing pulley 72 being attached to the coupling portion 70 of the wrist joint driving force transmission portion 48. Therefore, winding and unwinding of the end effector operating cable 43 are not performed, and only the wrist joint 30 rotates. Further, when rotating the wrist joint 30 while causing the end effector 22 to perform the holding operation or the releasing operation, the control portion 81 performs, while rotating the coupling portion 70 by the wrist joint driving portion 38, a differential control operation of the end effector driving force transmission portion 47 such that the angular position of the end effector operating cable pulling pulley 67 around the axis L1 relative to (the end effector operating cable direction changing pulley 72 of) the rotating coupling portion 70 becomes a predetermined angular position. With this, the holding operation or releasing operation of the end effector 22 can be performed while rotating the end effector 22 around the axis L1.

When replacing a certain surgical tool with a different surgical tool during surgery, the base 23 is detached from the robot main body driving mechanism 51, and the surgical robot 1 including the certain surgical tool is pulled out from the guide pipe 6. Then, the surgical robot 1 including the different surgical tool is inserted into the guide pipe 6. As above, a part of the surgical tools can be replaced while maintaining the position of the other surgical robot including the surgical tool other than the surgical tool to be replaced and the position of the endoscope 101 in the vicinity of the treated part. Therefore, the surgical tool can be replaced quickly, and load on the body of the patient P can be reduced. Further, workload on the operator W can be reduced.

Further, the robot main body 2 can be detached from the robot main body driving mechanism 51 and subjected to a sterilization treatment such as autoclave sterilization. To be specific, since the robot main body driving mechanism 51 includes electric devices such as a servo motor, the robot main body driving mechanism 51 is not suitable for the sterilization treatment such as the autoclave sterilization. By separating such robot main body driving mechanism 51 from the robot main body 2 not including any electric device, the robot main body 2 that contacts the patient P can be surely subjected to the sterilization treatment.

As explained above, the surgical robot 1 of the present invention is configured such that the base 23 can be detached from the robot main body driving mechanism 51, and therefore, the driving force transmission mechanism 24 and the robot main body driving mechanism 51 can be separated from each other. On this account, the robot main body 2 can be detached from the robot main body driving mechanism 51 and subjected to the sterilization treatment such as the autoclave sterilization. To be specific, since the robot main body driving mechanism 51 includes the electric devices such as the servo motor, the robot main body driving mechanism 51 is not suitable for the sterilization treatment such as the autoclave sterilization. By separating such robot main body driving mechanism 51 from the robot main body 2 not including any electric device, the robot main body 2 that contacts the patient P can be surely subjected to the sterilization treatment. Therefore, the surgical tool can be replaced quickly, and load on the body of the patient P can be reduced. Further, workload on the operator W can be reduced.

By attaching the base 23 to the robot main body driving mechanism 51, the wrist joint driving portion 38 is connected to the proximal end 44a of the torque transmission tube 44 through the coupling portion 70 and the driven-side wrist joint driving rotating body 71, and thus, the wrist joint driving portion 38 can rotate the torque transmission tube 44 around the axis of the torque transmission tube 44. With this, the end effector 22 provided at the distal end 21b of the arm 21 can be rotated around the axis L2 of the distal end 21b of the arm 21. Therefore, an angular position of the end effector 22 around the axis L2 can be changed. On this account, the operability of the surgical robot 1 can be improved even when the arm 21 is bent.

Modified Example

In the above embodiment, outer diameters (diameters of addendum circles) of the driven-side end effector driving rotating body 68 and the driven-side wrist joint driving rotating body 71 are substantially equal to each other. However, the above embodiment is not limited to this. The driven-side wrist joint driving rotating body 71 and the driven-side end effector driving rotating body 68 may be formed such that the outer diameter of the driven-side wrist joint driving rotating body 71 is larger than the outer diameter of the driven-side end effector driving rotating body 68. With this, the base 23 can be easily attached to and detached from the robot main body driving mechanism 51. Further, in this case, rotating speeds of the driven-side end effector driving rotating body 68 and the driven-side wrist joint driving rotating body 71 may be synchronized with each other by adjusting rotating speeds of the driving-side wrist joint driving rotating body 93 and the driving-side end effector driving rotating body 94. With this, only the wrist joint 30 can be rotated.

In the above embodiment, the driven-side engagement portions 62a are two projections, and the driven-side engagement portions 65a are two projections. Further, the driving-side engagement portions 91a are two depressions engaged with the driven-side engagement portions 62a, and the driving-side engagement portions 92a are two depressions engaged with the driven-side engagement portions 65a. However, the above embodiment is not limited to this. Instead of this, the driven-side engagement portions 62a may be constituted by one elongated projection extending in a radial direction, and the driven-side engagement portions 65a may be constituted by one elongated projection extending in a radial direction. Further, the driving-side engagement portions 91a may be constituted by one elongated depression extending in a radial direction and engaged with the driven-side engagement portions 62a, and the driving-side engagement portions 92a may be constituted by one elongated depression extending in a radial direction and engaged with the driven-side engagement portions 65a.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

REFERENCE SIGNS LIST 1 surgical robot
2 robot main body
3 driving portion
4 control unit
5 operating portion
6 guide pipe
21 arm
22 end effector
23 base
24 driving force transmission mechanism
25 flexible shaft
26 joint portion
27 first bending joint
28 second bending joint
29 connecting portion
30 wrist joint
31 frame member
32 operating cable coupling portion
33 operating cable coupling portion
35 first bending joint driving portion
36 second bending joint driving portion
37 end effector driving portion
38 wrist joint driving portion
41 first bending joint operating cable
42 second bending joint operating cable
43 end effector operating cable
44 torque transmission tube
45 first bending joint driving force transmission portion
46 second bending joint driving force transmission portion
47 end effector driving force transmission portion
48 wrist joint driving force transmission portion
50 driving portion casing
51 robot main body driving mechanism
61 first bending joint operating cable pulling pulley
62 driven-side first bending joint driving rotating body
63 first rotating shaft
64 second bending joint operating cable pulling pulley
65 driven-side second bending joint driving rotating body
66 second rotating shaft
67 end effector operating cable pulling pulley
68 driven-side end effector driving rotating body
69 third rotating shaft
70 coupling portion
71 driven-side wrist joint driving rotating body
72 end effector operating cable direction changing pulley
75 tubular portion
76 driving portion-side end plate
77 arm-side end plate
78 first bending joint operating cable direction changing pulley 79 second bending joint operating cable direction changing pulley
81 control portion
82 storage portion
91 driving-side first bending joint rotating body
92 driving-side second bending joint rotating body
93 driving-side wrist joint driving rotating body
94 driving-side end effector driving rotating body
100 surgical robot system
101 endoscope

The invention claimed is:

1. A surgical robot comprising:
a robot main body driving mechanism including:
a wrist joint driving portion having a first motor and a driving side wrist joint driving rotating body configured to be rotated by the first motor; and
an end effector driving portion having a second motor and a driving-side end effector driving rotating body configured to be rotated by the second motor; and
a robot main body including:
a base detachably attached to the robot main body driving mechanism;
an arm including a hollow shaft and a wrist joint, the hollow shaft including a proximal end continuous with the base, the wrist joint being continuous with a distal end of the hollow shaft and being configured to rotate about an axis of a distal end of the arm;
an end effector attached to the wrist joint;
a wrist joint driving force transmission portion including a hollow torque transmission tube disposed within the hollow shaft, the hollow torque transmission tube including:
a distal end attached to the wrist joint;
a coupling portion connected to the proximal end of the hollow torque transmission tube; and
a driven-side wrist joint rotating body connected to the coupling portion; and
an end effector driving force transmission portion including:
an end effector operating cable within the hollow torque transmission tube and having a distal end attached to the end effector;
a rotating shaft;
an end effector operating cable pulling pulley mounted to the rotating shaft and configured to be attached to a proximal end of the end effector operating cable; and
a driven-side end effector driving body connected to the rotating shaft,
wherein:
upon attaching the base to the robot main body driving mechanism, the driven-side wrist joint driving rotating body is engaged with the driving-side wrist joint driving rotating body and the driven-side end effector driving rotating body is engaged with the driving side end effector driving rotating body; and
upon detaching the base from the robot main body driving mechanism, the driven-side wrist joint driving rotating body is separated from the driving-side wrist joint driving rotating body and the driven-side end effector driving rotating body is separated from the driving-side end effector driving rotating body.

2. The surgical robot according to claim 1, wherein the shaft and the hollow torque transmission tube are flexible.

3. The surgical robot according to claim 1, wherein:
the robot main body driving mechanism includes a bending joint driving portion having a third motor and a driving-side bending joint driving rotating body configured to be rotated by the third motor;
the arm includes a bending joint disposed between the hollow shaft and the wrist joint and configured to bend the arm;
the robot main body includes a bending joint driving force transmission portion;
the bending joint driving force transmission portion includes a bending joint operating cable, a bending joint operating cable pulling pulley, a second rotating shaft, and a driven-side bending joint driving rotating body;
the bending joint operating cable has a distal end attached to the bending joint;
the bending joint operating cable pulling pulley is mounted on the second rotating shaft and is configured to be attached to a proximal end of the bending joint operating cable;
the driven-side bending joint driving rotating body is connected to the second rotating shaft;
upon attaching the base to the robot main body driving mechanism, the driven-side bending joint driving rotating body is engaged with the driving-side bending joint driving rotating body; and
upon detaching the base from the robot main body driving mechanism, the driven-side bending joint driving rotating body is separated from the driving-side bending joint driving rotating body.

4. The surgical robot according to claim 3, wherein the bending joint operating cable is disposed in a space between the hollow shaft and the hollow torque transmission tube.

5. The surgical robot according to claim 3, wherein:
the robot main body driving mechanism includes a second bending joint driving portion including a fourth motor and a second driving-side bending joint driving rotating body configured to be rotated by the fourth motor;
the arm includes a second bending joint provided between the hollow shaft and the bending joint and configured to bend the arm;
the robot main body includes a second bending joint driving force transmission portion;
the second bending joint driving force transmission portion includes a second bending joint operating cable, a second bending joint operating cable pulling pulley, a third rotating shaft, and a second driven-side bending joint driving rotating body;
the second bending joint operating cable has a distal end attached to the second bending joint;
the second bending joint operating cable pulling pulley is mounted on the third rotating shaft and is configured to be attached a proximal end of the second bending joint operating cable;
the second driven-side bending joint driving rotating body is connected to the third rotating shaft;
upon attaching the base to the robot main body driving mechanism, the second driven-side bending joint driving rotating body is engaged with the second driving-side bending joint driving rotating body; and
upon detaching the base from the robot main body driving mechanism, the second driven-side bending joint driving rotating body is separated from the second driving-side bending joint driving rotating body.

6. The surgical robot according to claim 1, wherein the end effector is a pair of forceps.

7. A surgical robot comprising:
a robot main body driving mechanism including:
- a wrist joint driving portion including a first motor and a driving-side wrist joint driving rotating body configured to be rotated by the first motor; and
- an end effector driving portion including a second motor and a driving-side end effector driving rotating body configured to be rotated by the second motor; and a robot main body including:
- a base detachably attached to the robot main body driving mechanism;
- an arm including a hollow shaft and a wrist joint, the hollow shaft having a proximal end continuous with the base, the wrist joint being continuous with a distal end of the hollow shaft, the wrist joint being configured to rotate about an axis of a distal end of the arm;
- an end effector attached to the wrist joint;
- a wrist joint driving force transmission portion including a hollow torque transmission tube within the hollow shaft, the hollow torque transmission tube including:
  - a distal end attached to the wrist joint;
  - a coupling portion connected to a proximal end of the hollow torque transmission tube; and
  - a driven-side wrist joint driving rotating body connected to the coupling portion; and
- an end effector driving force transmission portion including:
  - an end effector operating cable within the hollow torque transmission tube and having a distal end attached to the end effector;
  - a rotating shaft;
  - an end effector operating cable pulling pulley mounted on the rotating shaft and configured to be attached to a proximal end of the end effector operating cable; and
  - a driven-side end effector driving rotating body connected to the rotating shaft;

wherein the wrist joint driving force transmission portion and the end effector driving force transmission portion are disposed on the base.

8. The surgical robot according to claim 7, wherein the hollow shaft and the hollow torque transmission tube are flexible.

9. The surgical robot according to claim 7, wherein:
the robot main body driving mechanism includes a bending joint driving portion having a third motor and a driving-side bending joint driving rotating body configured to be rotated by the third motor;
the arm includes a bending joint provided between the hollow shaft and the wrist joint, the bending joint being configured to bend the arm;
the robot main body includes a bending joint driving force transmission portion;
the bending joint driving force transmission portion includes (i) a bending joint operating cable, (ii) a bending joint operating cable pulling pulley, (iii) a second rotating shaft, and (iv) a driven-side bending joint driving rotating body;
the bending joint operating cable has a distal end attached to the bending joint;
the bending joint operating cable pulling pulley is mounted on the second rotating shaft and is configured to be attached to a proximal end of the bending joint operating cable; and
the driven-side bending joint driving rotating body is connected to the second rotating shaft.

10. The surgical robot according to claim 9, wherein the bending joint operating cable is disposed in a space between the hollow shaft and the hollow torque transmission tube.

11. A surgical robot system comprising:
a first surgical robot;
a second surgical robot; and
a collectively bundling pipe, wherein:
each one of the first surgical robot and the second surgical robot includes:
a robot main body driving mechanism including:
- a wrist joint driving portion having a first motor and a driving-side wrist joint driving rotating body configured to be rotated by the first motor, and
- an end effector driving portion having a second motor and a driving-side end effector driving rotating body configured to be rotated by the second motor; and a robot main body including:
- a base detachably attached to the robot main body driving mechanism,
- an arm including a hollow shaft and a wrist joint, the hollow shaft including a proximal end continuous with the base, the wrist joint being continuous with a distal end of the hollow shaft, the wrist joint rotating around an axis of a distal end of the arm,
- an end effector attached to the wrist joint,
- a wrist joint driving force transmission portion including:
  - a hollow torque transmission tube within the hollow shaft and having a distal end attached to the wrist joint,
  - a coupling portion connected to a proximal end of the hollow torque transmission tube, and
  - a driven-side wrist joint driving rotating body connected to the coupling portion, and
- an end effector driving force transmission portion including:
  - an end effector operating cable within the hollow torque transmission tube and having a distal end attached to the end effector,
  - a rotating shaft,
  - an end effector operating cable pulling pulley mounted on the rotating shaft and configured to attached a proximal end of the end effector operating cable, and
  - a driven-side end effector driving rotating body connected to the rotating shaft,
the wrist joint driving force transmission portion and the end effector driving force transmission portion are disposed on the base, and
the collectively bundling pipe bundles the hollow shaft of the first surgical robot and the hollow shaft of the second surgical robot.

12. The surgical robot according to claim 11, wherein the hollow shaft and the hollow torque transmission tube of each of the first surgical robot and the second surgical robot are flexible.

* * * * *